United States Patent
Wagner et al.

(10) Patent No.: US 10,353,084 B1
(45) Date of Patent: Jul. 16, 2019

(54) SYSTEMS AND METHODS FOR COOLING AN IMAGING SYSTEM

(71) Applicant: General Electric Company, Schenectady, NY (US)

(72) Inventors: Grant Richard Wagner, Milwaukee, WI (US); Adam Clark Nathan, Shorewood, WI (US); Matthew Jason Evangelist, Lake Mills, WI (US); Chad Allan Smith, Franklin, WI (US); Mark Alan Frontera, Hartland, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/943,573

(22) Filed: Apr. 2, 2018

(51) Int. Cl.
  *G01T 1/24* (2006.01)
  *A61B 6/03* (2006.01)
  *A61B 6/02* (2006.01)
  *A61B 6/00* (2006.01)

(52) U.S. Cl.
  CPC .............. *G01T 1/244* (2013.01); *A61B 6/037* (2013.01); *A61B 6/4488* (2013.01)

(58) Field of Classification Search
  CPC ........ A61B 6/037; A61B 6/4488; G01T 1/244
  See application file for complete search history.

(56) References Cited

U.S. PATENT DOCUMENTS

| | | | |
|---|---|---|---|
| 2006/0065848 A1 | 3/2006 | Ueno et al. | |
| 2013/0284936 A1* | 10/2013 | McBroom | G01R 33/481 250/363.03 |
| 2017/0059720 A1 | 3/2017 | McBroom et al. | |
| 2018/0059270 A1* | 3/2018 | Hefetz | G01T 1/244 |

FOREIGN PATENT DOCUMENTS

CN   106901772 A   6/2017

* cited by examiner

*Primary Examiner* — Mark R Gaworecki
(74) *Attorney, Agent, or Firm* — McCoy Russell LLP

(57) ABSTRACT

Methods and systems are provided for cooling systems for imaging systems. In one embodiment, a manifold assembly for an imaging system comprises: an intake manifold and a return manifold formed by a plurality of unitary sections, the intake manifold and return manifold positioned adjacent to each other and separated by a shared wall; and a plurality of nozzles, with each nozzle of the plurality of nozzles formed by a corresponding section of the plurality of unitary sections. In this way, an assembly difficulty, expense, and/or manufacturing time of the manifold assembly may be decreased.

19 Claims, 12 Drawing Sheets

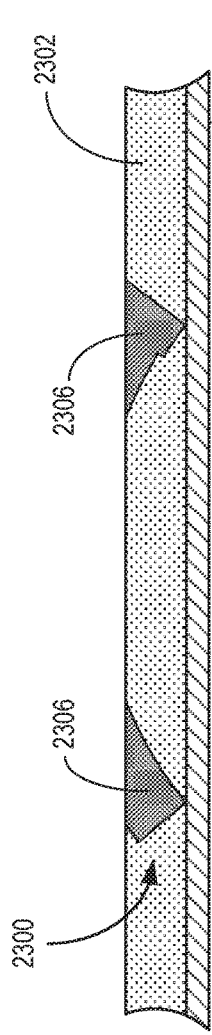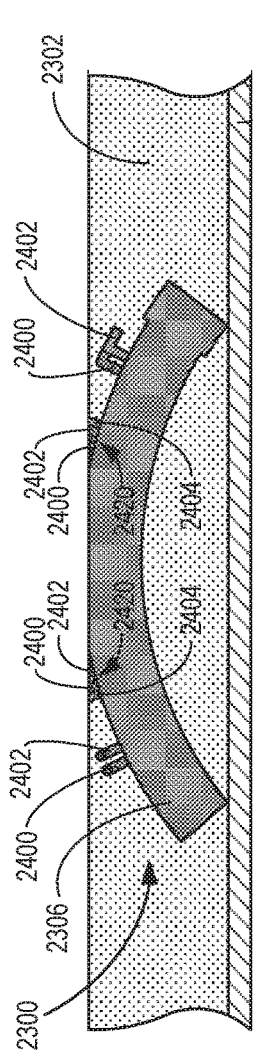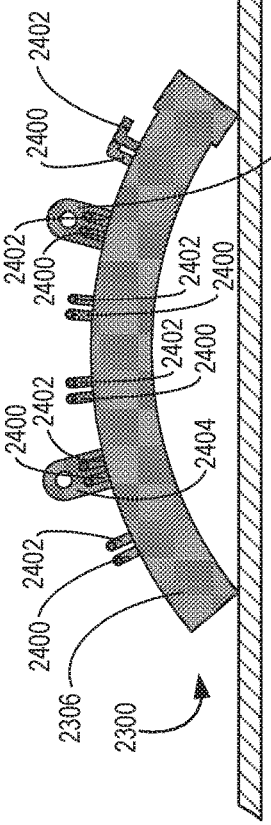

SYSTEMS AND METHODS FOR COOLING AN IMAGING SYSTEM

FIELD

Embodiments of the subject matter disclosed herein relate to imaging systems, and more particularly, to cooling systems for positron emission tomography (PET) systems.

BACKGROUND

Positron emission tomography (PET) systems generate images that represent a distribution of positron-emitting nuclides within a body of a patient. When a positron interacts with an electron by annihilation, the entire mass of a positron-electron pair is converted into two photons. The photons are emitted in opposite directions along a line of response (LOR). The annihilation photons are detected by detectors that are placed on both sides of the line of response, in a configuration such as a detector array or detector ring. The detectors convert the incident photons into useful electrical signals that can be used for image formation. An image thus generated based on the acquired image data includes the annihilation photon detection information. Often, such PET systems may be integrated together with a computed tomography (CT) system to form a dual-modality imaging system (PET/CT imaging system).

The detectors included by PET or PET/CT systems are often arrays of photodiodes, such as silicon photomultipliers (SiPMs), that detect light impulses from an array of scintillation crystals. The detectors are often mounted in close proximity to readout electronics to preserve a signal integrity of the photodiodes. In operation, the readout electronics generate heat that may affect the operation of the photodiodes. Accordingly, it is desirable to provide cooling for the detectors.

BRIEF DESCRIPTION

In one embodiment, a manifold assembly for a positron emission tomography (PET) system comprises: an intake manifold and a return manifold formed by a plurality of unitary sections, the intake manifold and return manifold positioned adjacent to each other and separated by a shared wall; and a plurality of nozzles, with each nozzle of the plurality of nozzles formed by a corresponding section of the plurality of unitary sections. In this way, the intake manifold, return manifold, nozzles, and other components of the manifold assembly are formed together as the plurality of unitary sections, resulting in a decreased number of separate components.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 23-25 show various steps of forming a unitary section of a manifold assembly for a cooling system of a PET/CT imaging system via an additive manufacturing process.

DETAILED DESCRIPTION

Figure 1:
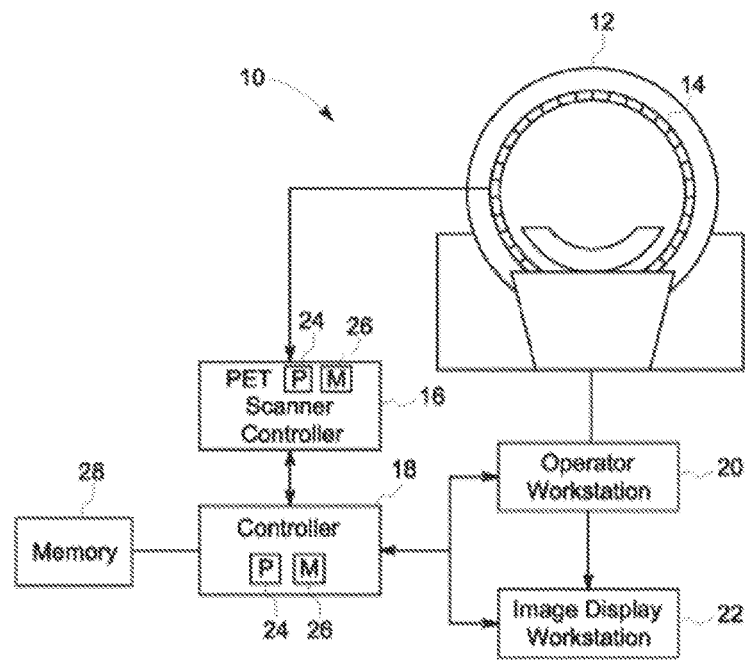
FIG. 1 shows a schematic representation of an embodiment of a positron emission tomography (PET) imaging system in accordance with aspects of the present disclosure.

The following description relates to various embodiments of imaging systems. In particular, systems and methods are provided for a cooling system for positron emission tomography (PET) systems. A PET system, such as the PET system shown by FIG. 1, may be incorporated together with a computed tomography (CT) system, such as the CT system shown by FIG. 2, to form a combined PET/CT system. The PET system includes a plurality of PET detectors positioned in an annular array encircling a bore of a gantry, and each PET detector may be cooled by a cooling system, such as the cooling system shown by FIG. 3. The cooling system includes a manifold assembly, such as the manifold assemblies shown by FIG. 4 and FIGS. 6-7, formed by a plurality of unitary sections, such as the sections shown by FIG. 5 and FIGS. 8-21. Each section is formed by an additive manufacturing process, such as the additive manufacturing process illustrated by the flow chart of FIG. 22 and the various steps shown by FIGS. 23-35.

Conventional cooling systems for the detectors may include separate coolant intake and return manifolds, with each of the manifolds including a plurality of components, such as nozzles, welded thereto to enable coolant to flow from the manifolds to the detectors and vice versa. Because PET and PET/CT systems may include a large number of detectors (e.g., more than thirty detectors), with each of the detectors fluidly coupled to the manifolds by separate nozzles, manufacturing the cooling systems by welding the nozzles and other components to the manifolds may increase an assembly difficulty, expense, and/or manufacturing time of the cooling systems.

The additive manufacturing process used to manufacture the manifold assemblies described herein enables each section of the manifold assemblies to be formed as a single, unitary piece relative to each other section, with each section including a plurality of components such as an intake passage, return passage, intake nozzles, return nozzles, and/or mounting brackets. The components are formed together (e.g., integrally formed) with each section via the additive manufacturing process, without welding or fusing of the components to the sections. Each section includes ends joined to adjacent sections in order to form the manifold assembly. Further, the sections may be manufactured with a variety of different shapes, sizes, and wall thicknesses that may be difficult or costly to achieve with other manufacturing processes. As a result, a cost and/or manufacturing time of the manifold assembly and cooling system may be reduced, and fluid flow characteristics and/or heat transfer characteristics of the manifold assembly may be increased.

Forming the components together as the plurality of unitary sections may reduce a manufacturing time and/or cost of the manifold assembly as described above, and may enable the intake manifold and return manifold to be produced with various different shapes, thicknesses, etc. to further reduce the cost and/or provide desirable flow characteristics to fluids disposed within the manifold assembly.

Though a PET system is described by way of example, it should be understood that the present techniques may also be useful when applied to imaging systems configured to acquire images by other imaging modalities, such as tomosynthesis, MM, C-arm angiography, and so forth. The present discussion of a PET imaging modality is provided merely as an example of one suitable imaging modality.

PET imaging is primarily used to measure metabolic activities that occur in tissues and organs and, in particular, to localize aberrant metabolic activity. In PET imaging, the subject is often injected with a solution that contains a radioactive tracer. The solution is distributed and absorbed throughout the body of the subject by different amounts, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits positrons that interact with and annihilate complementary electrons to generate pairs of gamma rays. In each annihilation reaction, two gamma rays traveling in opposite directions are emitted. In PET system 10 shown by FIGS. 1-2, the pair of gamma rays may be detected by detector array 12. Controller 18 may be configured to receive data (e.g., electrical signals) from the detector array 12, and may process the data in order to ascertain that two gamma rays detected by the detector array 12 that are detected sufficiently close in time (e.g., detected within a threshold amount of time relative to each other) are generated by a same annihilation reaction. Due to the nature of the annihilation reaction, the detection of such a pair of gamma rays may be used to determine a line of response along which the gamma rays traveled before impacting the detector (e.g., being detected by the detector array 12), enabling the controller 18 to determine that the annihilation event is localized to that line. By detecting a plurality of such gamma ray pairs, and calculating the corresponding lines traveled by these pairs via the controller 18, a concentration of the radioactive tracer in different parts of the body may be estimated. By examining the relative concentrations in the different parts of the body, a tumor may be detected. Therefore, accurate detection and localization of the gamma rays forms a fundamental and foremost objective of the PET system 10.

With the foregoing in mind and turning now to the drawings, FIG. 1 depicts positron emission tomography (PET) system 10 operating in accordance with certain aspects of the present disclosure. In some examples, the PET system 10 of FIG. 1 may be a dual-modality imaging system, such as a PET/computed tomography (CT) imaging described, as described further below with reference to FIG. 2.

The PET system 10 depicted in FIG. 1 includes detector array 12 (which may be referred to herein as a detector array). The detector array 12 of the PET system 10 may include a plurality of detector assemblies 14 (which may be referred to herein as detector modules and/or photodetector assemblies) arranged in one or more rings, as depicted in FIG. 1. Each detector assembly 14 (e.g., PET detector assembly) may include a plurality of detector units (e.g., three detector units, five detector units, or a different number of detector units). Each detector unit (which may be referred to herein as PET detector units) may include one or more sensors (e.g., photodiode arrays) configured to sense (e.g., measure, detect, etc.) electromagnetic waves (e.g., radioactive emissions) emitted from a body of a subject (e.g., a patient) scanned by the PET system 10. As described in greater detail below, each detector assembly 14 is configured to maintain the PET detector units (e.g., photodiode arrays) within a pre-determined operational temperature range (e.g., between 19° C. and 21° C.) to maintain a desired imaging quality of the PET system 10.

The depicted PET system 10 additionally includes a PET scanner controller 16, controller 18, an operator workstation 20, and an image display workstation 22 (e.g., a computer monitor or other graphical display device for displaying images produced by the PET system 10). In certain embodiments, two or more of the PET scanner controller 16, controller 18, operator work station 20, and image display workstation 22 may be combined into a single unit or device. The PET scanner controller 16, which is coupled to the detector array 12, may be coupled to the controller 18 to enable the controller 18 to control operation of the PET scanner controller 16. Additionally and/or alternatively, the PET scanner controller 16 may be coupled to the operator workstation 20 to enable the operator workstation 20 to control operation of the PET scanner controller 16. In operation, the controller 18 and/or the workstation 20 may control the real-time operation of the PET system 10. In some examples, the controller 18 and/or the workstation 20 may additionally control the real-time operation of another imaging modality (e.g., the CT imaging system shown by FIG. 2 and described below) to enable the simultaneous and/or separate acquisition of image data from the different imaging modalities.

One or more of the PET scanner controller 16, the controller 18, and/or the operation workstation 20 may include a computer processor 24 and/or computer memory 26 (e.g., random access memory and/or read-only memory). In certain embodiments, the PET system 10 may include a separate memory 28 (e.g., separate from computer memory 26). The detector array 12, PET scanner controller 16, the controller 18, and/or the operation workstation 20 may include detector acquisition circuitry for acquiring image data from the detector array 12 (e.g., for receiving electrical signals from the sensors of the detector units), image reconstruction and processing circuitry for image processing, and/or circuitry for regulating a temperature of the detector units of the detector assemblies 14 (e.g., independently regulating the temperature of each detector assembly 14 relative to each other detector assembly 14). The circuitry may include programmed hardware, memory, and/or processors.

The processor 24 may include multiple microprocessors, one or more general-purpose microprocessors, one or more special-purpose microprocessors, and/or one or more application specific integrated circuits (ASICS), system-on-chip (SoC) devices, or a different processor configuration. For example, the processor 24 may include one or more reduced instruction set (RISC) processors or complex instruction set (CISC) processors. The processor 24 may execute instructions stored in non-transitory memory (e.g., memory 26 and/or memory 28) to carry out the operation of the PET system 10. These instructions may be encoded in programs or code stored in a tangible non-transitory computer-readable medium (e.g., an optical disc, solid state device, chip, firmware, etc.), such as the memory 26 and/or memory 28. In certain embodiments, the memory 26 and/or memory 28 may be wholly or partially removable from the PET scanner controller 16 and/or controller 18.

Figure 2:
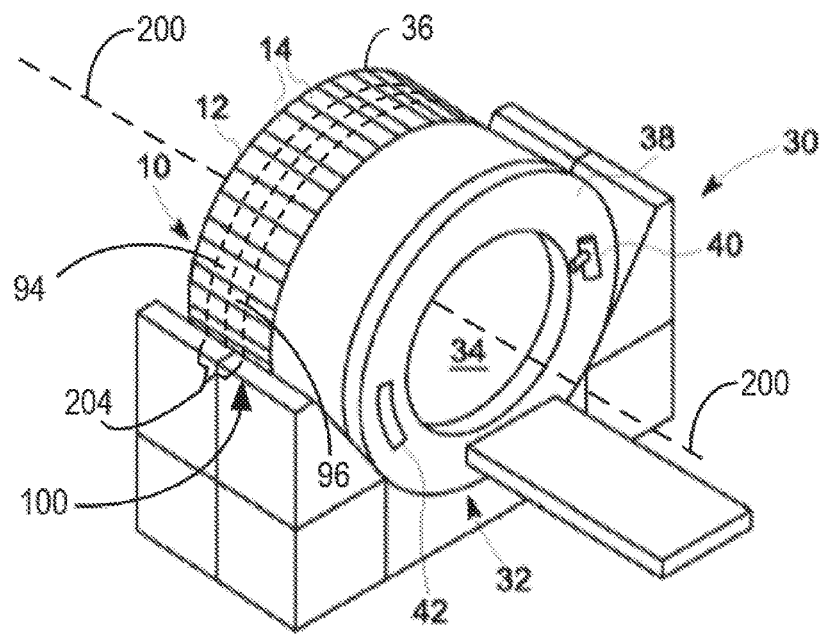
FIG. 2 shows a perspective view of a PET/computed tomography (CT) imaging system having the PET imaging system of FIG. 1.

As mentioned above, the PET system 10 may be incorporated into a dual-modality imaging system such as the PET/CT imaging system 30 shown by FIG. 2. PET/CT imaging system 30 includes the PET system 10 and a CT system 32 coupled to each other (e.g., positioned in fixed relationship to one another). The PET system 10 and CT system 32 are aligned with each other to enable translation of subject (e.g., a patient, not shown) therethrough (e.g., to enable the subject to be moved to a position in which the subject is within both of the PET system 10 and CT system 32. For example, the subject may be positioned within a bore 34 of the PET/CT imaging system 30 for imaging of a region of interest of the subject via the PET/CT imaging system 30.

The PET system 10 includes a gantry 36 that is configured to support the full ring annular detector array 12 thereon (e.g., including the plurality of detector assemblies 14 described above with reference to FIG. 1). The detector array 12 is positioned around the bore 34 (which may be referred to herein as a central opening) and can be controlled (e.g., controlled via controller 18) to perform an emission scan in which positron annihilation events are counted (e.g., measured). The detector assemblies 14 forming detector array 12 may generally generate intensity output signals (e.g., electrical signals having different amplitudes and/or frequencies) corresponding to each detected photon resulting from the positron annihilation events.

The CT system 32 includes a rotatable gantry 38 having an X-ray source 40 thereon that may be controlled by the controller 18 to project a beam of X-rays toward a CT detector assembly 42 on an opposite side of the gantry 38 (e.g., with the X-ray source 40 being positioned at a first side of the gantry 38 and the CT detector assembly 42 being positioned at an opposite, second side of the gantry 38). The CT detector assembly 42 may sense the projected X-rays that pass through the subject to be imaged and may measure an intensity of the X-ray beam after the beam has passed through the subject.

During a scan to acquire X-ray projection data (e.g., a scan in which the X-ray beam described above is projected through a region of interest of the subject in order to image the region), gantry 38 and the components mounted thereon may rotate about a center of rotation (e.g., rotate around central axis 200 of the PET/CT imaging system 30). In some examples, the CT system 32 may be controlled by the controller 18 and/or operator workstation 20 described above with reference to FIG. 1. In certain embodiments, the PET system 10 and the CT system 32 may share a single gantry. Image data may be acquired simultaneously and/or separately with the PET system 10 and the CT system 32.

PET system 10 further includes a cooling system 100. Cooling system 100 includes a manifold assembly 204 indicated schematically in FIG. 2. The manifold assembly 204 includes an intake manifold 94 (which includes an annular intake passage) and a return manifold 96 (which includes an annular return passage). The intake manifold 94 is configured to receive coolant from an outlet of a heat exchanger (e.g., outlet 306 of heat exchanger 106 described below with reference to FIG. 3). Coolant within the intake manifold 94 flows through the annular intake passage to the detector array 12, where the coolant may receive heat from components of the detector array 12 and may cool the components of the detector array 12. The heated coolant then flows from the detector array 12 to the annular return passage of the return manifold 96, and the heated coolant flows from the annular return passage to an inlet of the heat exchanger (e.g., inlet 304 of heat exchanger 106 shown by FIG. 3).

The heat exchanger is configured such that coolant flowing into the inlet of the heat exchanger is cooled by the heat exchanger prior to flowing out of the outlet of the heat exchanger toward the intake passage of the manifold assembly 204. In one example, the heat exchanger may include a plurality of fins configured to transfer heat from the coolant flowing into the inlet of the heat exchanger to atmospheric air surrounding the heat exchanger. In other examples, the heat exchanger may include different components configured to reduce a temperature of the coolant flowing into the inlet (e.g., one or more fans, fluid passages adapted to receive a second type of coolant, etc.). Additional aspects of the cooling system 100 are described below with reference to FIG. 3.

Figure 3:
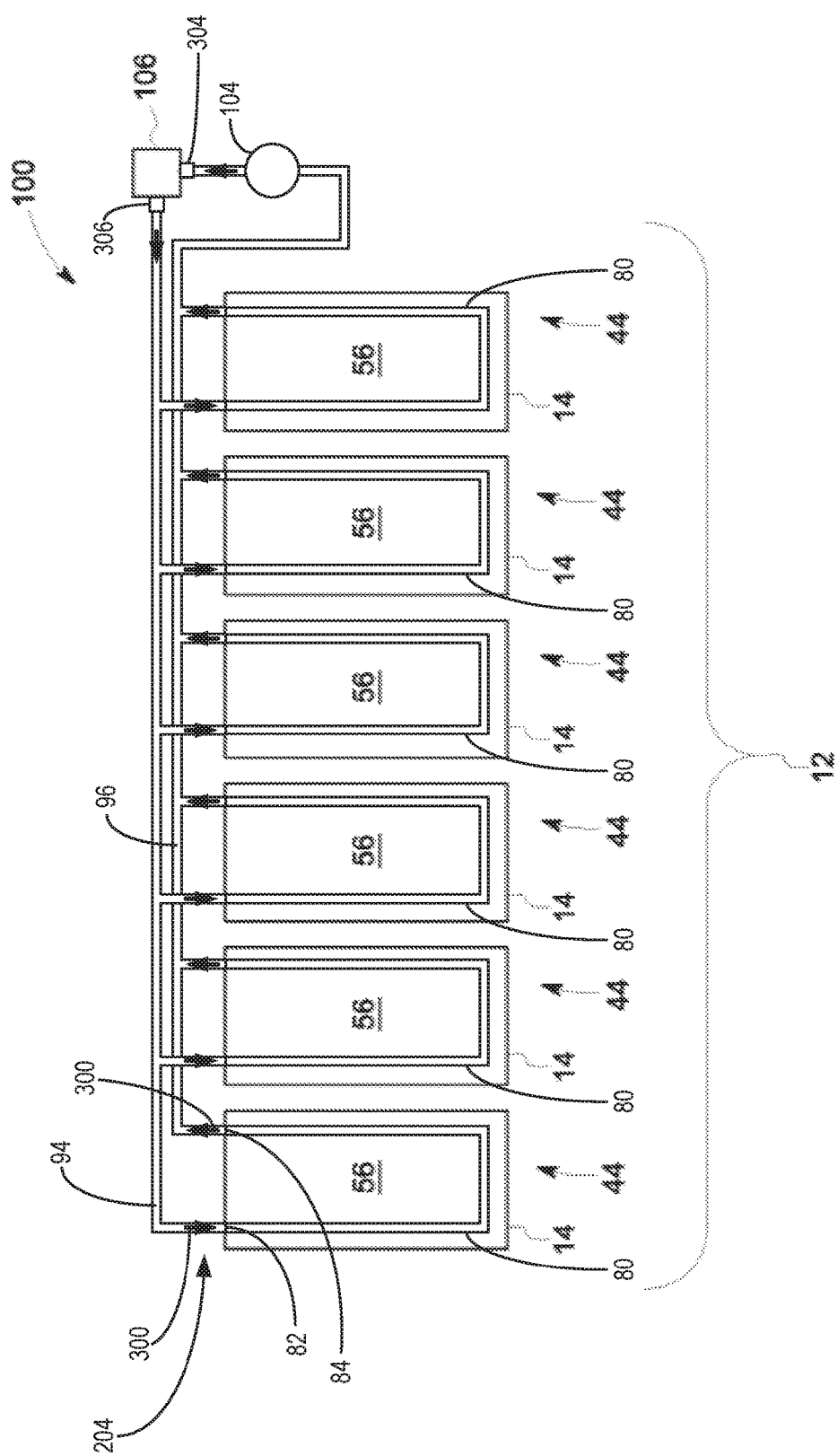
FIG. 3 shows a schematic illustration of a cooling system included by a PET/CT imaging system.

FIG. 3 shows a schematic illustration of cooling system 100. Cooling system 100 is utilized to provide coolant (e.g., cooling fluid, such as water) to respective thermally conductive plates 56 (which may be referred to herein as cold plates and/or cooling plates) included by the plurality of detector assemblies 14 of the detector array 12. As illustrated schematically by FIG. 3, intake manifold 94 and return manifold 96 are each coupled to the cold plates 56. Specifically, each cold plate 56 includes an inlet 82 fluidly coupled to (e.g., in fluidic communication with) the annular intake passage of intake manifold 94, and each cold plate 56 includes an outlet 84 fluidly coupled to (e.g., in fluidic communication with) the annular return passage of return manifold 96. In this configuration, with regard to each cold plate, coolant flows from the annular intake passage of intake manifold 94 into the inlet 82, through an internal passage 80 (which may be referred to herein as a cooling tube) disposed within the cold plate 56, and out of the outlet 84 to the annular return passage of return manifold 96, as indicated by arrows 300. Coolant from the outlets 84 may mix and/or converge within the annular return passage of the return manifold 96.

The cooling system 100 may further include a pump 104 configured to flow coolant from the heat exchanger 106 to the annular intake passage of the intake manifold 94, and/or to flow coolant from the annular return passage of the return manifold 96 to the heat exchanger. In operation, the pump 104 is configured to channel (e.g., flow) the coolant through each of the cold plates 56. The coolant facilitates reducing the operational temperature of the cold plates 56 which in turn reduces the operational temperature of the detector units 44. In one example, each cold plate 56 may be coupled in face-sharing contact with a corresponding detector unit of the detector array (e.g., the detector units described above with reference to FIG. 2). Specifically, surfaces each cold plate 56 may directly contact surfaces of the corresponding detector unit with no components positioned therebetween in order to enable heat to flow from the corresponding detector unit to the cold plate 56. The heat transferred from the detector unit to the cold plate 56 may then be absorbed by the coolant flowing through the internal passage 80 of the cold plate 56.

After the coolant has absorbed the latent heat from the cold plate 56, thus increasing the temperature of the coolant, the coolant is channeled through the heat exchanger 106. Although FIG. 3 illustrates six detector assemblies 14 coupled to the intake manifold 94 and return manifold 96, in some examples a different number of detector assemblies 14 (e.g., sixteen detector assemblies, thirty-two detector assemblies, etc.) may be coupled to the intake manifold 94 and return manifold 96 and cooled in a manner similar to the example shown by FIG. 3.

Figure 4:
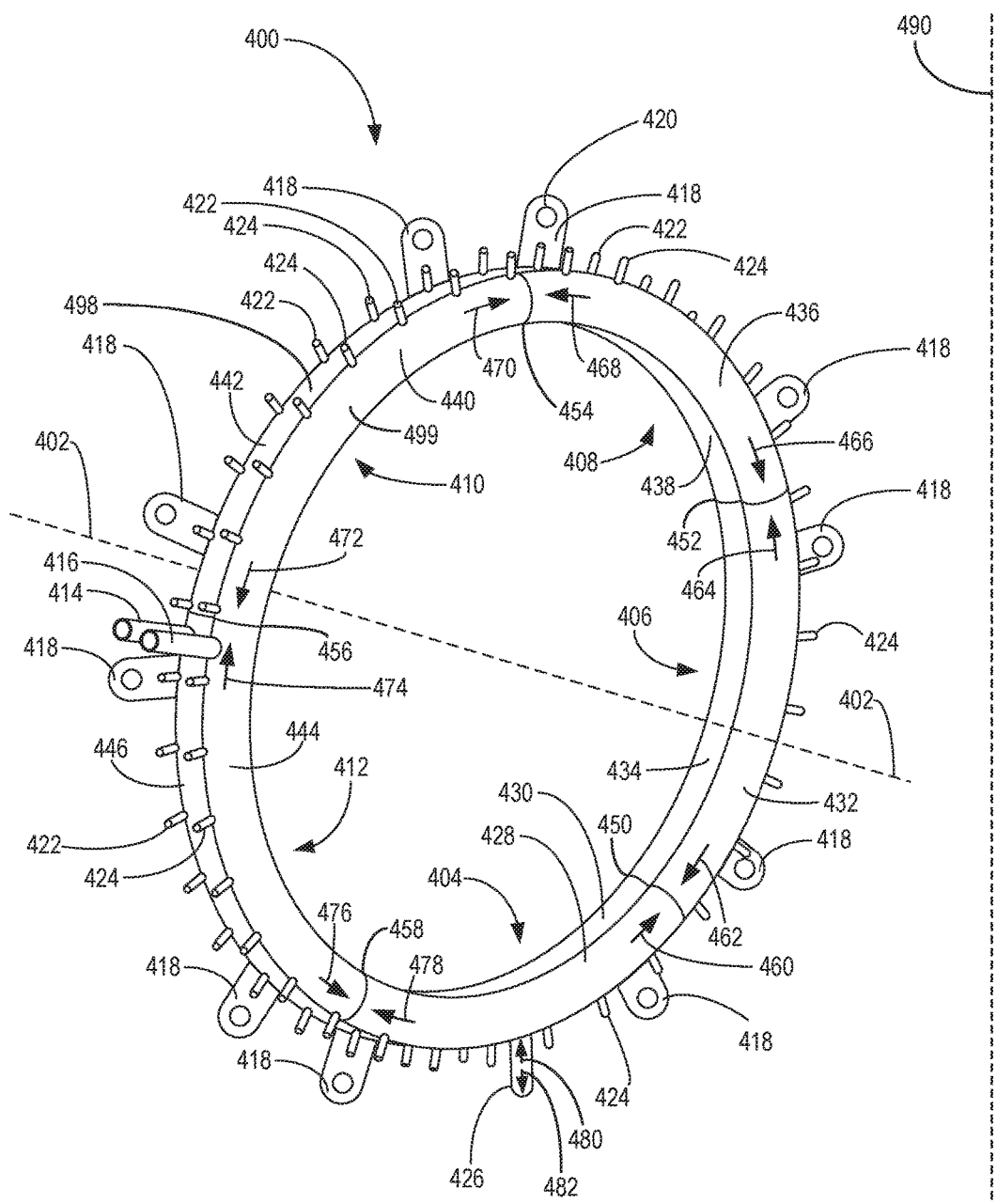
FIG. 4 shows a perspective view of a cooling manifold for a cooling system of a PET/CT imaging system.

FIG. 4 shows a perspective view of a manifold assembly 400 for a cooling system of an imaging system (e.g., the cooling system 100 of the PET/CT imaging system 30 shown by FIGS. 2-3 and described above). In one example, the manifold assembly 400 is similar to the manifold assembly 204 described above with reference to FIGS. 2-3.

Manifold assembly 400 includes a plurality of sections joined to each other around a central axis 402 of the manifold assembly 400. Specifically, the manifold assembly 400 shown by FIG. 4 includes a first section 404, a second section 406, a third section 408, a fourth section 410, and a fifth section 412. However, in other examples, the manifold assembly 400 may include a different number of sections (e.g., six, seven, eight, etc.). The first section 404 includes a return passage 428 and an intake passage 430, the second section 406 includes a return passage 432 and an intake passage 434, the third section 408 includes a return passage 436 and an intake passage 438, the fourth section 410 includes a return passage 440 and an intake passage 442, and the fifth section 412 includes a return passage 444 and an intake passage 446.

The intake passage of each section is separated from the return passage of each section by one or more walls (which may be referred to herein as arcuate walls), such that fluids do not flow directly from the intake passage to the return passage during conditions in which the manifold assembly 400 is assembled. For example, the first section 404 includes the intake passage 430 and the return passage 428 as described above. However, the intake passage 430 and return passage 428 are separated from each other by the one or more walls (e.g., internal or interior walls) such that fluids disposed within the intake passage 430 (e.g., coolant, such as water) do not flow directly from the intake passage 430 to the return passage 428, and fluids disposed within the return passage 428 do not flow directly from the return passage 428 to the intake passage 430.

During conditions in which the first section 404, second section 406, third section 408, fourth section 410, and fifth section 412 are coupled together, the intake passage 430, intake passage 434, intake passage 438, intake passage 442, and intake passage 446 (which may be referred to herein as arcuate intake passages) form a single, annular intake passage of intake manifold 498. The annular intake passage may be similar to the annular intake passage described above with reference to intake manifold 94 of FIGS. 2-3. For example, during conditions in which the manifold assembly 400 is coupled to an imaging system such as the PET/CT imaging system 30 shown by FIG. 2 and described above, the annular intake passage formed by the intake passages 430, 434, 438, 442, and 446 may surround a bore of the imaging system adapted to receive a subject to be imaged (e.g., bore 34). The central axis 402 of the manifold assembly 400 may be parallel and/or coaxial with an axis of the subject (e.g., an axis extending from a head of the subject to feet of the subject), and the annular intake passage (and intake manifold 498) may encircle the subject and central axis 402.

Similarly, during conditions in which the first section 404, second section 406, third section 408, fourth section 410, and fifth section 412 are coupled together, the return passage 428, return passage 432, return passage 436, return passage 440, and return passage 444 (which may be referred to herein as arcuate return passages) are fluidly coupled to (e.g., in fluidic communication with) each other to form a single, annular return passage of return manifold 499 of the manifold assembly 400. The annular return passage may be similar to the return passage described above with reference to the return manifold 96 of FIGS. 2-3. For example, during conditions in which the manifold assembly 400 is coupled to an imaging system such as the PET/CT imaging system 30 shown by FIG. 2 and described above, the annular return passage formed by the return passages 428, 432, 436, 440, and 444 may surround a bore of the imaging system adapted to receive a subject to be imaged (e.g., bore 34). The central axis 402 of the manifold assembly 400 may be parallel and/or coaxial with an axis of the subject (e.g., an axis extending from a head of the subject to feet of the subject), and the annular return passage (and return manifold 499) may encircle the subject and central axis 402.

The annular intake passage of intake manifold 498 and annular return passage of return manifold 499 are separated by a shared wall formed by the arcuate walls, with the shared wall forming inner surfaces of each of the annular return passage and annular intake passage. For example, the shared wall may be shaped as an annular wall separating the annular intake passage and annular return passage and formed by each of the arcuate walls. Further, the shared wall joins the intake manifold 498 to the return manifold 499, such that the intake manifold 498 is not removable from the return manifold 499 (and vice versa). Said another way, the intake manifold 498 and return manifold 499 are not separate components. Instead, each of the intake manifold 498 and return manifold 499 are formed together by the plurality of sections (e.g., first section 404, second section 406, third section 408, fourth section 410, and fifth section 412) and are positioned adjacent to each other (e.g., centered relative to central axis 402 and including one or more shared walls). However, the shared wall fluidly isolates the annular intake passage from the annular return passage, similar to the example of the intake passage 430 being fluidly separated from the return passage 428 as described above.

Each of the first section 404, second section 406, third section 408, fourth section 410, and fifth section 412 has an arcuate shape and includes a first end and an opposing, second end. Specifically, first section 404 includes first end 460 and second end 478, second section 406 includes first end 464 and second end 462, third section 408 includes first end 468 and second end 466, fourth section 410 includes first end 472 and second end 470, and fifth section 412 includes first end 476 and second end 474. In the configuration shown by FIG. 4, each section is positioned between two different, adjacent sections. For example, first section 404 is positioned between and adjacent to fifth section 412 and second section 406, second section 406 is positioned between and adjacent to first section 404 and third section 408, third section 408 is positioned between and adjacent to second section 406 and fourth section 410, fourth section 410 is positioned between and adjacent to third section 408 and fifth section 412, and fifth section 412 is positioned between and adjacent to fourth section 410 and first section 404.

Because each of the sections has the arcuate shape (e.g., arcuate cross-section in a plane, with central axis 402 extending in a normal direction of the plane), during conditions in which the sections are assembled with each other (e.g., joined to each other) to form the manifold assembly 400, the resulting manifold assembly 400 has an annular shape and includes the return manifold 499 having the annular return passage and the intake manifold 498 having the annular intake passage as described above. In one example, in order to join the sections together to form the manifold assembly 400, the ends of each section may be fused (e.g., welded) to ends of each adjacent section. For example, as shown by FIG. 4, first end 460 of first section 404 is fused to second end 462 of second section 406 as indicated by joint 450, first end 464 of second section 406 is fused to second end 466 of third section 408 as indicated by joint 452, first end 468 of third section 408 is fused to second end 470 of fourth section 410 as indicated by joint 454, first end 472 of fourth section 410 is fused to second end 474 of fifth section 412 as indicated by joint 456, and first end 476 of fifth section 412 is fused to second end 478 of first section 404 as indicated by joint 458. In some examples, such as the example shown by FIG. 6 and described below, the ends of each section (e.g., first end 460 and second end 478 of first section 404, first end 464 and second end 462 of second section 406, etc.) may be shaped to enable each section to couple with each adjacent section without fusing the ends of the sections together.

Each section (e.g., first section 404, second section 406, third section 408, fourth section 410, and fifth section 412) is formed as a unitary piece relative to each other section. For example, as described below, each of the sections includes a plurality of components configured to couple the sections to a detector array of the imaging system (e.g., detector array 12 described above with reference to FIGS. 1-3). With regard to the first section 404, components of the first section 404 configured to couple the first section 404 to the detector array are formed together as a unitary piece with each other portion of the first section 404. Similarly, components of the second section 406 configured to couple the second section 406 to the detector array are formed together as a unitary piece with each other portion of the second section 406. The third section 408, fourth section 410, and fifth section 412 are formed in a similar way. In one example, each of the first section 404, second section 406, third section 408, fourth section 410, and fifth section 412 are formed via an additive manufacturing process such as 3D printing.

The manifold assembly 400 includes an intake inlet 414 and a return outlet 416. Intake inlet 414 is configured to fluidly couple the manifold assembly 400 to an outlet of a coolant source (e.g., the outlet 306 of the heat exchanger 106 described above with reference to FIG. 3), and return outlet 416 is configured to fluidly couple the manifold assembly 400 to an inlet of the coolant source (e.g., inlet 304 of heat exchanger 106). In this configuration, coolant flows from the outlet of the coolant source into the manifold assembly 400 via the intake inlet 414, and coolant flows out of the manifold assembly 400 via the return outlet 416 to the inlet of the coolant source. In the example shown by FIG. 4, each of the intake inlet 414 and return outlet 416 are positioned at the fifth section 412. The intake inlet 414 and return outlet 416 are formed together (e.g., integrally formed) with the fifth section 412 via the additive manufacturing process, as described above. For example, the intake inlet 414 and return outlet 416 may be 3D printed together with each other component of the fifth section 412 as a single piece (e.g., the intake inlet 414 and return outlet 416 are not separate components that are fused, fastened, etc. to the fifth section 412). In other examples, however, the intake inlet 414 and return outlet 416 may be positioned at a different section of the manifold assembly 400, and may be formed together with the different section. For example, the intake inlet 414 and return outlet 416 may instead be formed as components of the third section 408, with the third section 408, intake inlet 414, and return outlet 416 being integrally formed as a single, unitary piece having a same material via the additive manufacturing process (e.g., the intake inlet 414 and return outlet 416 are not separate components that are fused, fastened, etc. to the third section 408).

In the example shown by FIG. 4, the manifold assembly 400 includes a plurality of brackets 418 (e.g., mounting brackets) formed by each of the sections (e.g., first section 404, second section 406, third section 408, fourth section 410, and fifth section 412). Each of the brackets 418 may include an opening 420 shaped to receive a fastener (e.g., a bolt, clamp, etc.). Each section of the manifold assembly 400 includes two brackets 418. However, in other examples, one or more of the sections may include a different number of brackets 418 relative to one or more other sections. For example, first section 404 may include one bracket, and each other section may include two brackets 418. In another example, the second section 406 and fifth section 412 may include three brackets 418, and the third section 408 may not include any brackets 418. Other examples are possible.

Similar to the intake inlet 414 and return outlet 416 described above, the brackets 418 are integrally formed with their corresponding sections via the additive manufacturing process. For example, as described above, the first section 404 is shown by FIG. 4 to include two brackets 418. Each of the two brackets included by the first section 404 are formed together with the first section 404 via the additive manufacturing process, such that the first section 404 and the two brackets 418 are together a single, unitary piece formed entirely of a same material (e.g., the brackets 418 are not fused, fastened, glued, etc. to the first section 404, and are formed of a same, continuous material as the first section 404). Similarly, the second section 406 is shown by FIG. 4 to include two brackets 418, and the two brackets 418 of the second section 406 are formed together with the second section 406 as a single, unitary piece via the additive manufacturing process.

The manifold assembly 400 further includes a plurality of intake nozzles 422 and return nozzles 424. Intake nozzles 422 are configured to provide coolant from the annular intake passage of the manifold assembly 400 (e.g., the annular intake passage formed by each of the intake passages 430, 434, 438, 442, and 446) to a plurality of cooling plates of the detector array of the imaging system (e.g., cold plates 56 shown by FIG. 3 and described above), and return nozzles 424 are configured to receive heated coolant from the plurality of cooling plates (e.g., from internal passages of the cooling plates similar to internal passage 80 of cold plates 56) and to flow the heated coolant into the annular return passage of the manifold assembly 400 (e.g., the annular return passage formed by each of the return passages 428, 432, 436, 440, and 444).

Intake nozzles 422 are positioned along intake passages 430, 434, 438, 442, and 446, and extend in outward directions relative to central axis 402 and exterior surfaces of the intake passages 430, 434, 438, 442, and 446. Said another way, each of the intake nozzles 422 extends radially outward from an intake passage which it is coupled to, relative to central axis 402. Each of the intake nozzles 422 includes an opening (e.g., similar to openings 515 shown by FIG. 5) fluidly coupled to (e.g., in fluidic communication with) an interior of the annular intake passage, such that fluids within the intake nozzles 422 and the interior of the annular intake passage may mix and/or converge. For example, intake nozzles 422 of the first section 404 are fluidly coupled to an interior of the intake passage 430, intake nozzles 422 of the second section 406 are fluidly coupled to an interior of the intake passage 434, etc., with the interiors of each of the intake passages being fluidly coupled to each other to form the annular intake passage. Return nozzles 424 are positioned along return passages 428, 432, 436, 440, and 444, and extend in outward directions (e.g., radially outward) relative to central axis 402 and exterior surfaces of the return passages 428, 432, 436, 440, and 444. Each of the return nozzles 424 includes an opening (e.g., similar to openings 513 shown by FIG. 5) fluidly coupled to (e.g., in fluidic communication with) an interior of the annular return passage, such that fluids within the return nozzles 424 and the interior of the annular return passage may mix and/or converge. For example, return nozzles 424 of the first section 404 are fluidly coupled to an interior of the return passage 428, return nozzles of the second section 406 are fluidly coupled to an interior of the return passage 432, etc., with the interiors of each of the return passages being fluidly coupled to each other to form the annular return passage.

As described above, each of the sections of the manifold assembly 400 (e.g., first section 404, second section 406, third section 408, fourth section 410, and fifth section 412) is formed as a separate, unitary piece relative to each other section. Further, the intake nozzles 422 and return nozzles 424 of each section are formed together with their corresponding section via the additive manufacturing process described above. For example, the intake nozzles 422 and return nozzles 424 of the first section 404 are formed together with the intake passage 430 and return passage 428 of the first section 404, such that the intake nozzles 422, return nozzles 424, intake passage 430, and return passage 428 of the first section 404 are a single, seamless unit. The intake nozzles 422 of the first section 404 are not separate components relative to the intake passage 430 of the first section 404, and the return nozzles 424 of the first section 404 are not separate components relative to the return passage 428 of the first section 404 (e.g., the intake nozzles 422 and return nozzles 424 are not separate components that are fastened, fused, glued, etc. to other elements of the first section 404, such as intake passage 430 and return passage 428).

Although the first section 404 is described above with regard to being a unitary piece together with the intake nozzles 422 and return nozzles 424 of the first section 404, each other section of the manifold assembly similarly incorporates the intake nozzles 422 and return nozzles 424. For example, the intake nozzles 422, return nozzles 424, intake passage 434, and return passage 432 of the second section 406 are formed together as a single unitary piece via the additive manufacturing process, the intake nozzles 422, return nozzles 424, intake passage 438, and return passage 436 of the third section 408 are formed together as a single unitary piece via the additive manufacturing process, the intake nozzles 422, return nozzles 424, intake passage 442, and return passage 440 of the fourth section 410 are formed together as a single unitary piece via the additive manufacturing process, and the intake nozzles 422, return nozzles 424, intake passage 446, and return passage 444 of the fifth section 412 are formed together as a single unitary piece via the additive manufacturing process.

In some examples, one or more of the first section 404, second section 406, third section 408, fourth section 410, and fifth section 412 may include a different number of intake nozzles 422 and/or return nozzles 424 relative to one or more of the other sections. For example, the manifold assembly 400 may include a total of thirty-four intake nozzles 422 and thirty-four return nozzles 424, with the first section 404 including six intake nozzles 422 and six return nozzles 424, with the second section 406, third section 408, and fourth section 410 each including eight intake nozzles 422 and eight return nozzles 424, and with the fifth section 412 including four intake nozzles 422 and four return nozzles 424. In other examples, the manifold assembly 400 may include a different total number of intake nozzles 422 and/or a different total number of return nozzles 424, and/or may include a different number of intake nozzles 422 and/or return nozzles 424 for each section relative to the example described above.

In some examples (such as the examples shown by FIGS. 5-6 and described below), a shape of the intake nozzles 422 and/or return nozzles 424 may be different than the example shown by FIG. 4. For example, the intake nozzles 422 and/or return nozzles 424 may include one or more bends (e.g., angled portions or curved portions). Further, one or more of the intake nozzles 422 may be shaped differently (e.g., angled differently) relative to one or more other intake nozzles 422, and/or one or more return nozzles 424 may be shaped differently (e.g., angled differently) relative to one or more other return nozzles 424.

The manifold assembly 400 includes a drain outlet 426 formed by (e.g., integrally formed with, via the additive manufacturing process) the first section 404. In some examples, the drain outlet 426 may be fluidly coupled to one or each of the intake passage 430 and return passage 428 (e.g., coupled to the intake passage 430 and/or return passage 428 at a first end 480 of the drain outlet 426), and the drain outlet 426 may be sealed (e.g., sealed at an opposite, second end 482 of the drain outlet 426) via a sealing mechanism (e.g., a valve, plug, cover, etc.). In other examples, each of the intake passage 430 and return passage 428 may include separate drain outlets, with the drain outlets being fluidly isolated from each other. In yet other examples, only one of the intake passage 430 or the return passage 428 may include the drain outlet 426 (e.g., only one of the intake passage 430 or return passage 428 may be fluidly coupled to the drain outlet 426).

During conditions in which the drain outlet 426 is sealed by the sealing mechanism, coolant disposed within the intake passage 430 does not flow out of the intake passage 430 via the drain outlet 426 (e.g., does not flow out of the annular intake passage via drain outlet 426), and coolant disposed within the return passage 428 does not flow out of the return passage 428 via the drain outlet 426 (e.g., does not flow out of the annular return passage via the drain outlet 426). However, during conditions in which the drain outlet 426 is unsealed (e.g., not sealed by the sealing mechanism), coolant disposed within the intake passage 430 and/or the return passage 428 may flow out of the manifold assembly 400 via the drain outlet 426. For example, during conditions in which the manifold assembly 400 is coupled to the imaging system (e.g., by mounting the manifold assembly 400 to the imaging system via the brackets 418), the drain outlet 426 may be positioned at a lower vertical position (e.g., relative to a direction of gravity, indicated by vertical axis 490) than each of the annular intake passage and the annular return passage to enable coolant to drain from the annular intake passage and/or the annular return passage through the drain outlet 426 via gravity while the drain outlet 426 is unsealed (e.g., gravity may provide the driving force for the drainage of the coolant through the drain outlet 426). Said another way, the drain outlet 426 may be positioned at a bottom of the manifold assembly 400 with respect to a ground surface on which the imaging system including the manifold assembly 400 sits. In this configuration, the drain outlet 426 increases an ease with which coolant may be removed from the manifold assembly 400 (e.g., for maintenance and/or repair of the manifold assembly 400, for removal of the manifold assembly 400 from the imaging system, etc.).

In the example shown by FIG. 4, the drain outlet 426 is formed together (e.g., integrally formed) along with the intake passage 430, return passage 428, intake nozzles 422, and return nozzles 424 of the first section 404 via the additive manufacturing process, such that the first section is a single, unitary piece comprising the drain outlet 426, intake passage 430, return passage 428, intake nozzles 422, and return nozzles 424 formed entirely of a same material (e.g., stainless steel). The drain outlet 426 is not a separate piece relative to the other components of the first section 404, and the drain outlet 426 is not fused, fastened, glued, etc. to the first section 404. Instead, the drain outlet 426, intake passage 430, return passage 428, intake nozzles 422, and return nozzles 424 of the first section 404 are formed of a same, continuous material (e.g., stainless steel) via the additive manufacturing process.

Figure 5:
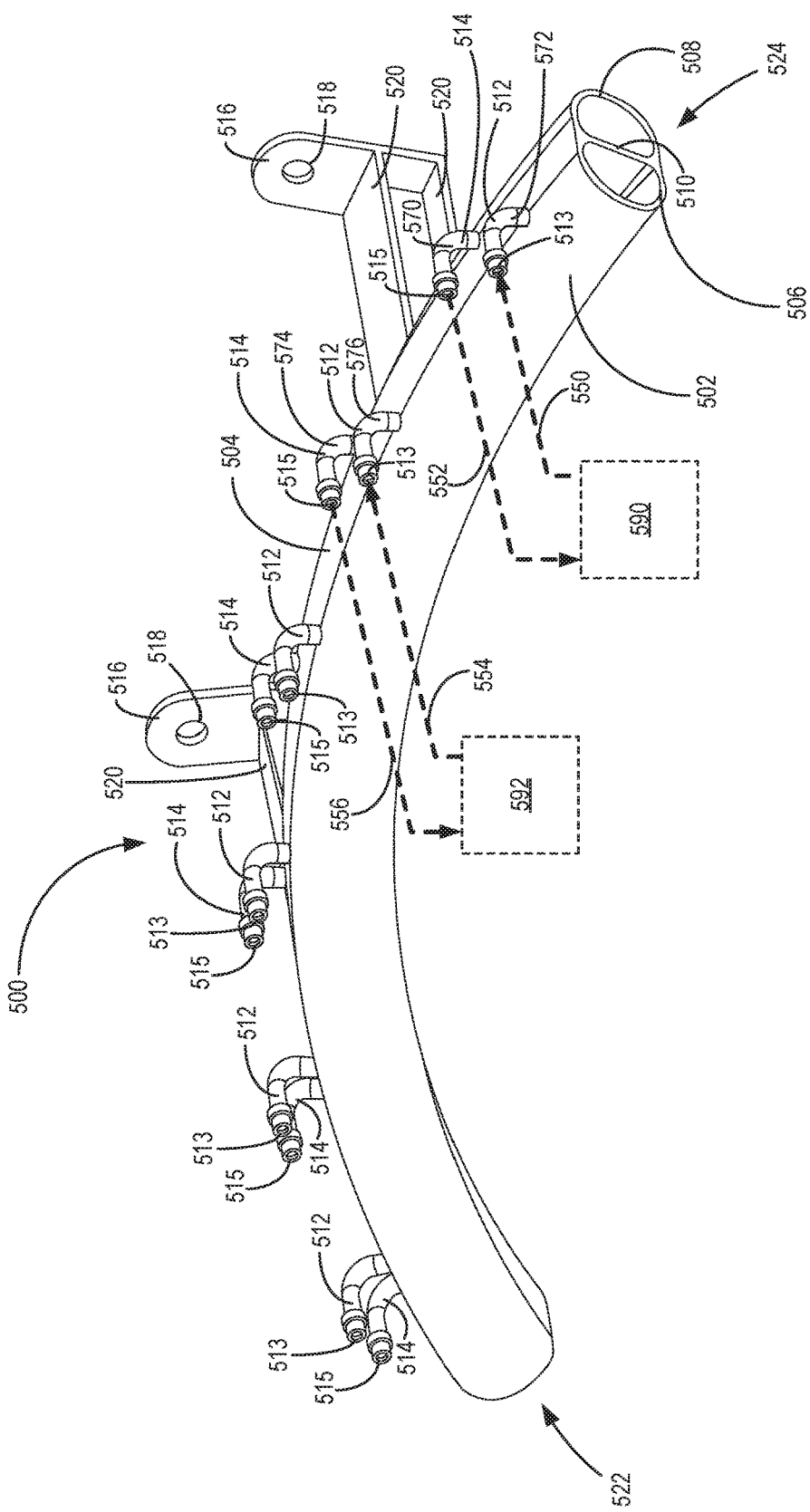
FIG. 5 shows a unitary section of a cooling manifold for a PET/CT imaging system, the unitary section formed by an additive manufacturing process.

Turning now to FIG. 5, a perspective view of a section 500 of a manifold assembly (e.g., manifold assembly 400 described above with reference to FIG. 4) for an imaging system (e.g., PET/CT imaging system 30 shown by FIG. 2 and described above) is shown. The section 500 includes an arcuate return passage 502 and an arcuate intake passage 504 (e.g., exactly one arcuate return passage 502 and exactly one arcuate intake passage 504), with the return passage 502 and intake passage 504 extending between a first end 522 and a second end 524 of the section 500 (e.g., similar to the first end 460 and second end 478 of first section 404 described above with reference to FIG. 4, in one example). The intake passage 504 forms openings 508 at each of the first end 522 and second end 524, and the return passage 502 forms openings 506 at each of the first end 522 and second end 524. During conditions in which the section 500 is joined to other sections to form the manifold assembly (e.g., as described above with reference to first section 404, second section 406, third section 408, fourth section 410, and fifth section 412 being assembled to form the annular intake passage and annular return passage of manifold assembly 400), the openings 508 fluidly couple the intake passage 504 to intake passages of adjacent sections (e.g., sections of the manifold assembly joined to the section 500), and openings 506 fluidly couple the return passage 502 to return passages of the adjacent sections.

Return passage 502 and intake passage 504 are formed together as a single, unitary piece via the additive manufacturing process described above with reference to FIG. 4. The return passage 502 and intake passage 504 are fluidly separated from each other by wall 510, such that fluid (e.g., coolant) disposed within the intake passage 504 does not flow directly to the return passage 502, or vice versa (e.g., wall 510 fluidly isolates return passage 502 from intake passage 504). In some examples, such as the examples described below with reference to FIGS. 8-21, the wall 510 may be shaped differently than shown by FIG. 5. The additive manufacturing process of the section 500 enables the return passage 502, intake passage 504, wall 510, and other components of the section 500 to be formed with a large variety of different shapes and/or configurations that may be difficult and/or costly to achieve with other types of manufacturing processes. For example, wall 510 (which may be referred to herein as an arcuate wall, similar to the arcuate walls described above with reference to FIG. 4) may formed via the additive manufacturing process to include a reservoir (e.g., a pocket), and in some examples, the reservoir may be adapted to store a thermally insulating material (e.g., foam) having a lower thermal conductivity than a material of the wall 510 (e.g., stainless steel). In other examples, the reservoir may be a vacuum reservoir, with the thermally insulating material stored in the reservoir being a gas (e.g., air) having a very low pressure relative to atmospheric pressure (e.g., $10^{-6}$ atm). In yet further examples, the reservoir may be fluidly coupled to atmospheric air, with the atmospheric air having a lower thermal conductivity than a material of the wall 510. Further examples are possible, such as the examples shown by FIGS. 8-21 described further below.

Similar to the sections of the manifold assembly 400 described above with reference to FIG. 4, the section 500 shown by FIG. 5 includes a plurality of intake nozzles 514 fluidly coupled to intake passage 504 and a plurality of return nozzles 512 fluidly coupled to return passage 502. Each of the intake nozzles 514 includes an opening 515 adapted to fluidly couple the interior of the intake passage 504 to an inlet of an internal passage of a cooling plate of the imaging system (e.g., inlet 82 of internal passage 80 of cold plate 56 shown by FIG. 3 and described above). Specifically, each intake nozzle 514 may be coupled to a corresponding inlet of a corresponding cold plate, such that each intake nozzle 514 is coupled to a different inlet of a different cold plate relative to each other intake nozzle 514 (e.g., similar to the configuration shown by FIG. 3 and described above).

Each of the return nozzles 512 includes an opening 513 adapted to fluidly couple the interior of the return passage 502 to a corresponding outlet of a corresponding internal passage of a corresponding cooling plate of the imaging system (e.g., outlet 84 of internal passage 80 of cold plate 56 shown by FIG. 3 and described above). Specifically, each return nozzle 512 may be coupled to a corresponding outlet of a corresponding cold plate, such that each return nozzle 512 is coupled to a different outlet of a different cold plate relative to each other return nozzle 512 (e.g., similar to the configuration shown by FIG. 3 and described above).

Figure 7:
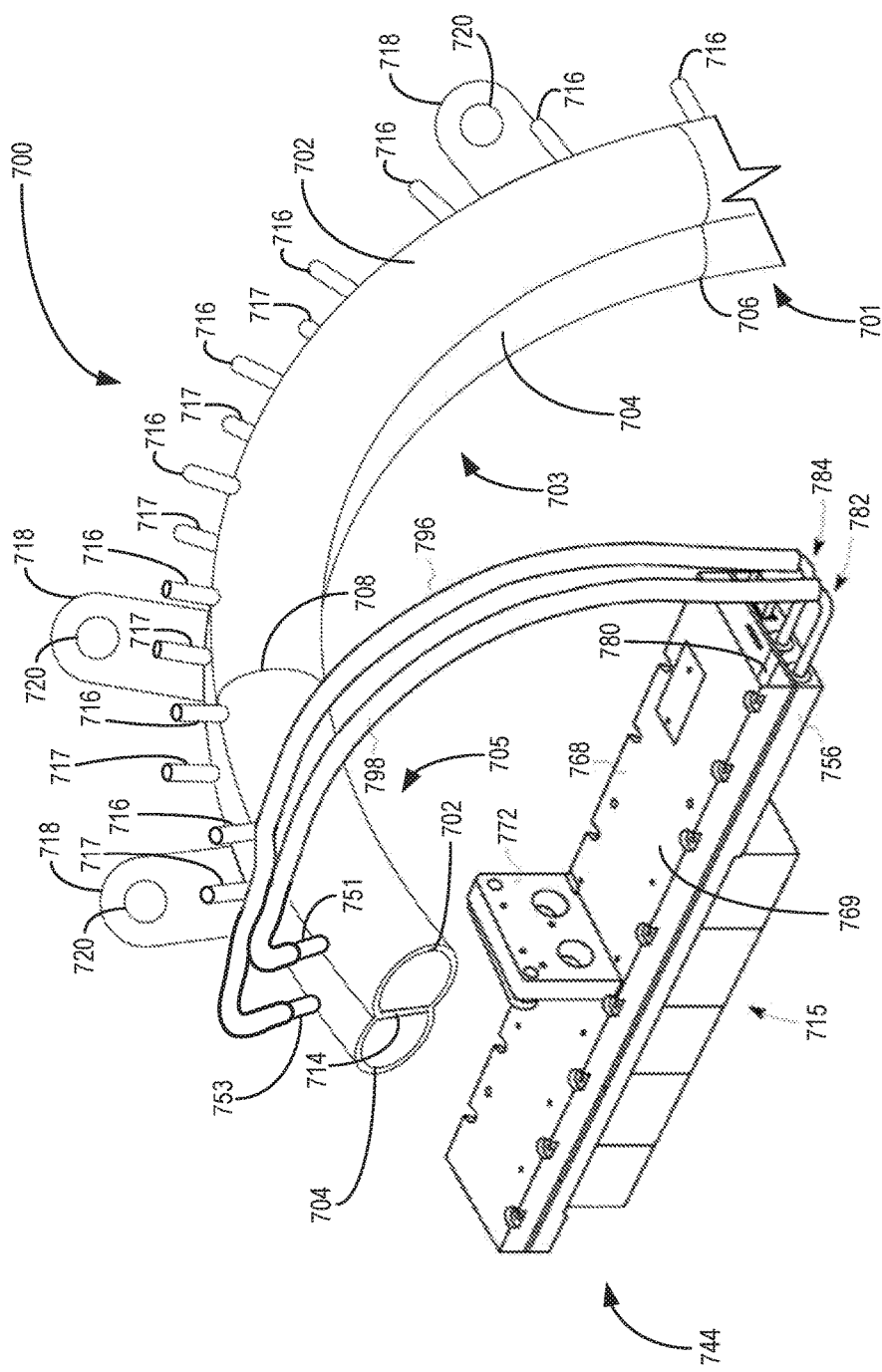
FIG. 7 shows a perspective view of a PET detector assembly coupled to a cooling manifold for a PET/CT imaging system, the cooling manifold including a plurality of unitary sections formed by an additive manufacturing process.

As an example of coolant flow through the intake nozzles 514 and return nozzles 512, FIG. 5 includes arrows 550, 552, 554, and 556. Arrow 552 indicates a flow of coolant from a first intake nozzle 570 of the intake nozzles 514 to a first cooling plate (shown schematically at 590) of the imaging system, arrow 550 indicates a flow of coolant from the first cooling plate to a first return nozzle 572 of the return nozzles 512, arrow 556 indicates a flow of coolant from a second intake nozzle 574 of the intake nozzles 514 to a different, second cooling plate (shown schematically at 592) of the imaging system, and arrow 554 indicates a flow of coolant from the second cooling plate of the imaging system to a second return nozzle 576 of the return nozzles 512. A similar configuration is shown by FIG. 7 and described further below.

The section 500 includes a plurality of brackets 516, with each of the brackets 516 including an opening 518. As described above with reference to the brackets 418 of manifold assembly 400, the brackets 516 are formed together with other components of the section 500 via the additive manufacturing process. Specifically, the intake nozzles 514, return nozzles 512, intake passage 504, return passage 502, wall 510, and brackets 516 are formed together via the additive manufacturing process such that section 500 is a single, unitary piece, and each of the components of the section 500 may be formed of a same, continuous material via the additive manufacturing process.

During conditions in which the section 500 is coupled to other sections to form the manifold assembly (e.g., to form a joined intake manifold and return manifold, similar to intake manifold 498 and return manifold 499 of FIG. 4), the brackets 516 may couple the manifold assembly to the imaging system (e.g., couple the manifold assembly to an interior of a gantry of the imaging system, such as gantry 36 shown by FIG. 2). For example, one or more other sections of the manifold assembly may include brackets similar to the brackets 516, and fasteners (e.g., bolts) may be inserted through the openings 518 of the brackets 516 in order to couple the manifold assembly to the gantry. In some examples, one or more of the brackets 516 may be offset from the manifold assembly (e.g., spaced apart from the annular intake passage and annular return passage) via one or more arms, such as arms 520 of brackets 516 shown by FIG. 5. In the example shown by FIG. 5, the arms 520 extend away from the section 500 in a direction parallel to a central axis (e.g., central axis 402 shown by FIG. 4) of the manifold assembly during conditions in which the section 500 is joined to other sections to form the manifold assembly.

In other examples, one or more of the brackets may be angled relative to one or more other brackets. For example, section 500 may be formed via the additive manufacturing process to include a first bracket having arms positioned at a first angle relative to the central axis and a second bracket having arms positioned at a different, second angle relative to the central axis. Other sections of the manifold assembly may additionally include brackets positioned at different angles relative to the brackets of the section 500, with the brackets being formed together with their corresponding sections via the additive manufacturing process. In this configuration, the various sections of the manifold assembly (e.g., section 500) may be formed via the additive manufacturing process to include brackets having different relative angles, sizes, shapes, etc. in order to enable the manifold assembly to couple to a variety of different imaging systems (e.g., imaging systems having different size gantries, different interior mounting structures, etc.).

Figure 6:
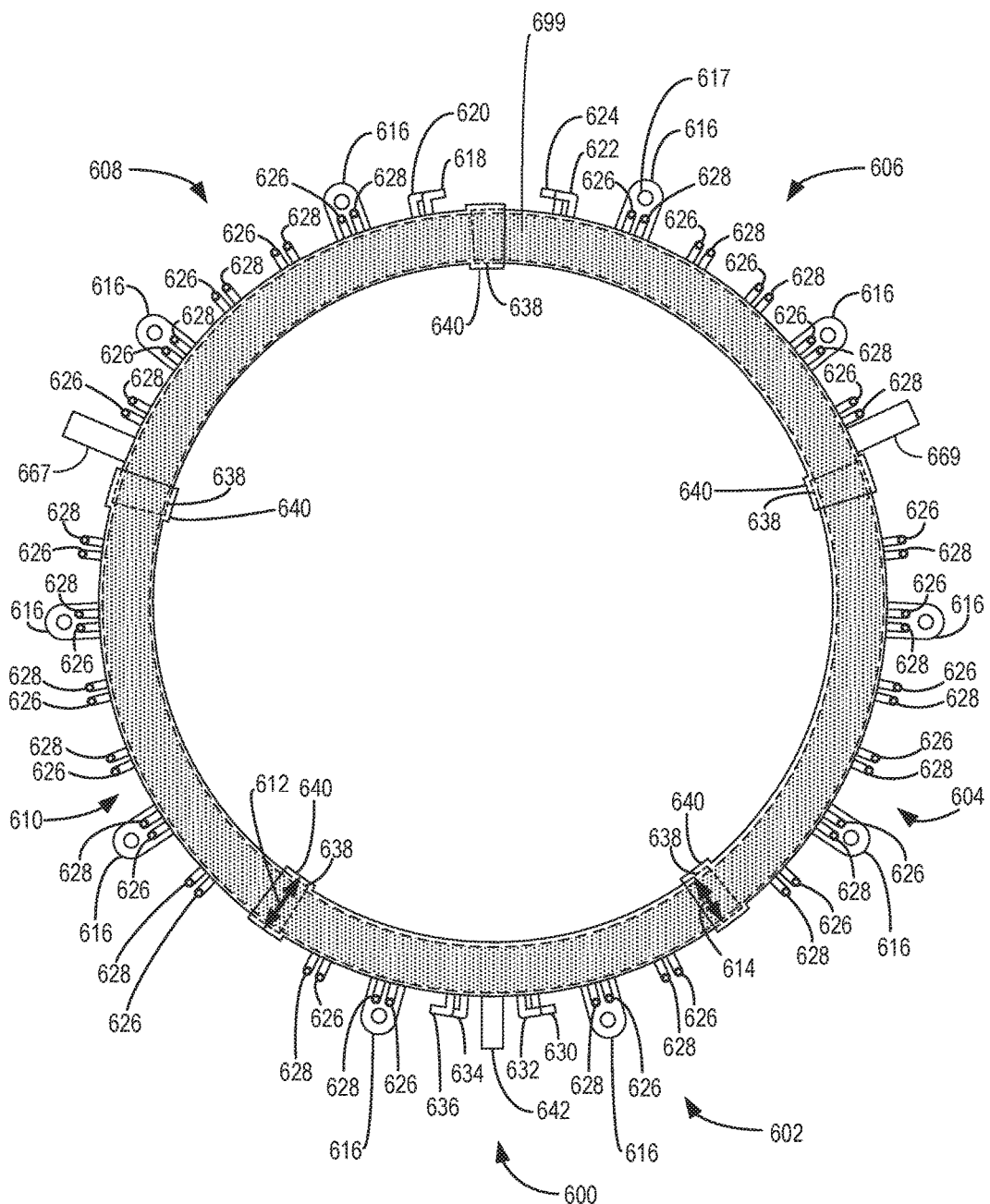
FIG. 6 shows a side view of a cooling manifold for a PET/CT imaging system, the cooling manifold including a plurality of unitary sections formed by an additive manufacturing process.

FIG. 6 shows another example of a manifold assembly 600 that may be included within an imaging system (e.g., the imaging systems described above with reference to FIGS. 1-3). Manifold assembly 600 includes a plurality of sections joined to each other, similar to the example of manifold assembly 400 described above with reference to FIG. 4. In some examples, one or more of the sections of the manifold assembly 600 may be similar to the section 500 described above with reference to FIG. 5. Each section of the manifold assembly 600 is formed as a separate, unitary piece via an additive manufacturing process, similar to the examples described above. The sections are joined to each other (e.g., after being formed separately via the additive manufacturing process) in order to form the manifold assembly 600.

Manifold assembly 600 includes first section 602, second section 604, third section 606, fourth section 608, and fifth section 610. In the example shown by FIG. 6, the sections of the manifold assembly 600 are coupled to each other without fusing, welding, etc. Specifically, each of the sections includes a first end 640 having a first width 612 (e.g., thickness or diameter) and a second end 638 having a second width 614 (e.g., thickness or diameter). The first width 612 is larger than the second width 614 (e.g., a greater amount of width) to enable the second end 638 of each section to fit within the first end 640 of a corresponding, adjacent section.

For example, as shown by FIG. 6, the second end 638 of the first section 602 is coupled to (e.g., disposed within) the first end 640 of the second section 604, the second end 638 of the second section 604 is coupled to the first end 640 of the third section 606, the second end 638 of the third section 606 is coupled to the first end 640 of the fourth section 608, the second end 638 of the fourth section 608 is coupled to the first end 640 of the fifth section 610, and the second end 638 of the fifth section 610 is coupled to the first end 640 of the first section 602. In this configuration, the first section 602, second section 604, third section 606, fourth section 608, and fifth section 610 form the manifold assembly 600. Each section includes an intake passage and a return passage (e.g., similar to intake passage 504 and return passage 502 described above with reference to section 500 of FIG. 5), with the intake passages of the sections joining to form an intake manifold having an annular intake passage, and with the return passages of the sections joining to form a return manifold having an annular return passage, with the intake manifold and return manifold including one or more shared walls (e.g., similar to the joined intake manifold 498 and return manifold 499 described above with reference to FIG. 4). The annular return passage of manifold assembly 600 is indicated schematically in FIG. 6 by shaded region 699, with the annular return passage being disposed within an interior of the manifold assembly 600. The annular intake passage has a similar, ring-like configuration. Further, one or more of the sections may include brackets 616 having openings 617, similar to the brackets 418 shown by FIG. 4 and/or the brackets 516 shown by FIG. 5.

In some examples, one or more gaskets may be disposed between the first end 640 and second end 638 of adjacent sections of the manifold assembly 600. For example, a gasket may be disposed between first end 640 of first section 602 and second end 638 of fifth section 610, such that the gasket surrounds the second end 638 of the fifth section 610 and is positioned within an interface between the second end 638 of the fifth section 610 and the first end 640 of the first section 602. The gasket may fluidly seal the interface such that fluids (e.g., coolant) disposed within the first section 602 and/or fifth section 610 do not flow out of the interface. In other examples, the first end 640 and second end 638 of adjacent sections of the manifold assembly 600 may be sealed in a different way (e.g., glued, fused, press-fit, etc.). Further, the first end 640 and second end 638 may be coupled together via one or more fasteners (e.g., grommets), in some examples.

The manifold assembly 600 includes a plurality of intake nozzles 626 (e.g., similar to the intake nozzles 422 of manifold assembly 400 shown by FIG. 4 and/or intake nozzles 514 of section 500 shown by FIG. 5) and a plurality of return nozzles 628 (e.g., similar to the return nozzles 424 of manifold assembly 400 shown by FIG. 4 and/or return nozzles 512 of section 500 shown by FIG. 5). In some examples, such as the example shown by FIG. 6, one or more of the intake nozzles 626 and/or return nozzles 628 may be angled relative to one or more other intake nozzles 626 and/or return nozzles 628. For example, first section 602 is shown to include a first intake nozzle 630 angled differently (e.g., in an opposite direction) relative to a second intake nozzle 634. First section 602 additionally includes a first return nozzle 632 angled differently (e.g., in an opposite direction) relative to a second return nozzle 636. The first intake nozzle 630, second intake nozzle 634, first return nozzle 632, and second return nozzle 636 are each angled differently relative to the intake nozzles 626 and return nozzles 628 of the sections adjacent to the first section 602 (e.g., fifth section 610 and second section 604). In one example, in the configuration of the first section 602 shown by FIG. 6, access to drain outlet 642 (e.g., similar to drain outlet 426 of manifold assembly 400 shown by FIG. 4) may be increased (e.g., for maintenance of manifold assembly 600) relative to configurations that do not include the differently angled intake nozzles and return nozzles.

Additionally and/or alternately, other sections of the manifold assembly 600 (e.g., other than first section 602) may include intake nozzles and return nozzles angled differently relative to other intake nozzles and return nozzles of the manifold assembly 600. For example, the third section 606 shown by FIG. 6 includes intake nozzle 624 and return nozzle 622 angled differently relative to each other intake nozzle 626 and return nozzle 628 of the third section 606. The fourth section 608 includes intake nozzle 620 and return nozzle 618 angled differently relative to each other intake nozzle 626 and return nozzle 628 of the fourth section 608. Further, intake nozzle 624 of third section 606 is angled in an opposite direction relative to intake nozzle 620 of fourth section 608, and return nozzle 622 of third section 606 is angled in an opposite direction relative to return nozzle 618 of the fourth section 608. In one example, angling the intake nozzles and return nozzles of the third section 606 and fourth section 608 according to the configuration shown by FIG. 6 may enable the nozzles to more effectively couple to one or more cooling plates of the imaging system (e.g., cooling plates 56 shown by FIG. 3 and described above).

Manifold assembly 600 additionally includes intake inlet 667 formed by fourth section 608, and return outlet 669 formed by third section 606. Intake inlet 667 and return outlet 669 may be similar to intake inlet 414 and return outlet 416, respectively, of manifold assembly 400 described above with reference to FIG. 4. However, instead of being included by a single section (e.g., fifth section 412) as shown by FIG. 4, the intake inlet 667 and return outlet 669 are each formed by different sections of the manifold assembly 600. In other examples, the intake inlet 667 and return outlet 669 may be formed by the same section (e.g., both formed by fourth section 608).

FIG. 7 shows a partial sectional view of a manifold assembly 700 for an imaging system (e.g., the PET/CT imaging system 30 shown by FIG. 2 and described above), similar to the manifold assemblies described above (e.g., manifold assembly 204 shown by FIGS. 2-3, manifold assembly 400 shown by FIG. 4, and/or manifold assembly 600 shown by FIG. 6). Manifold assembly 700 includes a plurality of unitary sections formed via an additive manufacturing process (e.g., similar to the sections described above, such as section 500) and joined to each other, such as section 701, section 703, and section 705. Section 701 is joined (e.g., fused) to section 703 as indicated by joint 706, and section 703 is joined (e.g., fused) to section 705 as indicated by joint 708. However, in some examples, the sections may be coupled together in a way similar to that described above with reference to FIG. 6 (e.g., with each section including a first end and a second end similar to first end 640 and second end 638, with the second end of each section fitting within the first end of a corresponding adjacent section).

The manifold assembly 700 includes several components similar to the components of the manifold assemblies described above. For example, manifold assembly 700 includes a plurality of return nozzles 716 similar to the return nozzles 424 of manifold assembly 400 of FIG. 4, return nozzles 512 of section 500 of FIG. 5, and/or return nozzles 628 of manifold assembly 600 of FIG. 6, a plurality of intake nozzles 717 similar to intake nozzles 422 of manifold assembly 400 of FIG. 4, intake nozzles 514 of section 500 of FIG. 5, and/or intake nozzles 626 of manifold assembly 600 of FIG. 6, and a plurality of brackets 718 having openings 720 similar to brackets 418 and openings 420 of manifold assembly 400 of FIG. 4, brackets 516 and openings 518 of section 500 of FIG. 5, and/or brackets 616 and openings 617 of manifold assembly 600 of FIG. 6. The manifold assembly 700 further includes an intake manifold having an annular intake passage formed by each intake passage of each section (e.g., intake passage 704 of section 705) of the manifold assembly 700 (e.g., similar to the annular intake passages described above), and the manifold assembly 700 includes a return manifold having an annular return passage formed by each return passage of each section (e.g., return passage 702 of section 705) of the manifold assembly 700 (e.g., similar to the annular return passages described above), with the intake manifold and return manifold joined to each other (e.g., similar to intake manifold 498 and return manifold 499 of FIG. 4). The annular intake passage and annular return passage (and likewise, the intake manifold and return manifold) are fluidly separated from each other by at least one wall of each section, such as wall 714 of section 705. In some examples, wall 714 may be similar to the walls shown by FIGS. 8-21.

In the example shown by FIG. 7, a first intake nozzle 753 (e.g., one of the plurality of intake nozzles 717) and a first return nozzle 751 (e.g., one of the plurality of return nozzles 716) form a nozzle set coupled to a detector assembly 715 of the imaging system via a first passage 796 and a second passage 798, respectively. In one example, the first passage 796 and second passage 798 are each flexible passages (e.g., tubing). In other examples, the first passage 796 and/or second passage 798 may be rigid passages (e.g., pipes). Detector assembly 715 may be similar to the detector assemblies 14 described above with reference to FIGS. 1-3 and may include several components similar to those included by detector assemblies 14. For example, detector assembly 715 includes an outlet 784, an inlet 782, a cold plate 756, an internal passage 780, and a plurality of detector units 744, similar to the outlet 84, inlet 82, cold plate 56, internal passage 80, and detector units 44, respectively, described above with reference to FIG. 3. The intake nozzles 717 and return nozzles 716 form a plurality of nozzle sets similar to the nozzle set described above, with each nozzle set including one intake nozzle and one return nozzle. Each nozzle set may be coupled to a separate, different detector assembly (e.g., detector assemblies similar to detector assembly 715) relative to each other nozzle set.

The detector assembly 715 may further include a cover 768 and mounting tab 772. In some examples, cover 768 is disposed over readout electronics of the detector assembly 715 and may substantially seal the readout electronics within a cavity of the cover 768. The cover 768 may be fabricated from aluminum, with the cavity formed by the cover 768 and the cold plate 756 forming a radio frequency shield (e.g., Faraday Cage) to substantially block or reduce electromagnetic interference from external sources from causing undesirable interference with the operation of the readout electronics. The cover 768 may be secured or coupled to the cold plate 756 using a plurality of mechanical fasteners (e.g., threaded bolts). In some examples, the cover 768 includes mounting tab 772, and the mounting tab 772 may extend outward from the cover 768 in a normal direction of an exterior surface 769 of the cover 768. The mounting tab 772 may enable the detector assembly 715 to be more easily mounted within a detector array (e.g., detector array 12 described above with reference to FIGS. 1-3. The mounting tab 772 may be formed from a material (e.g., stainless steel) having a lower thermal conductivity than the cold plate 756 (which may be formed of a material having a relatively higher thermal conductivity, such as copper). The mounting tab 772 may provide support for the detector assembly 715 during conditions in which the detector assembly 715 is mounted to the imaging system (e.g., as part of the detector array), and the material of the mounting tab 772 may reduce a likelihood of transferring heat away from the cold plate 756 and/or cover 768 via the mounting tab 772.

Turning now to FIGS. 8-21, cross-sectional views of different sections for manifold assemblies are shown. Each of the sections shown by FIGS. 8-21 are formed by an additive manufacturing process (e.g., 3D printing) as single, unitary pieces, similar to the examples of the sections described above (e.g., section 500 shown by FIG. 5). For example, material forming each of the sections shown by FIGS. 8-21 is continuous (e.g., does not include welds or other fusing) due to the additive manufacturing process, and as a result, a strength of the sections may be increased. Further, the sections may be more easily formed with various shapes and/or cross-sections that may be difficult to achieve with other manufacturing processes (e.g., welding of separate components to form the sections). For example, a thickness of one or more walls of the sections may be reduced relative to conventional manifolds that include welded and/or fused intake nozzles, return nozzles, brackets, etc., enabling the sections to be produced more quickly and/or with a reduced cost (e.g., with a reduced amount of material). For example, with regard to conventional manifolds for cooling systems of PET/CT systems, welding intake nozzles and return nozzles to the manifolds may not be successful unless the manifolds and/or nozzles have a sufficient thickness (e.g., wall thickness) for joining the material (e.g., metal) of the walls with the material of the intake nozzles and return nozzles. For example, some conventional manifolds include walls having a first thickness (e.g., 3 millimeters), and nozzles having a smaller, second thickness (e.g., 1.5 millimeters). Welding the nozzles to the walls may result in degradation of the nozzles and/or walls due to the different thicknesses.

However, with regard to the manifold assemblies described herein (and the sections described herein, such as the sections described below with reference to FIGS. 8-21), because each section is formed as a separate, unitary piece along with its corresponding intake nozzles, return nozzles, brackets, etc., a thickness of the walls forming the intake passage, return passage, intake nozzles, return nozzles, brackets, etc. of each section may be reduced (e.g., reduced relative to conventional manifolds), which may reduce an amount of material consumed to produce the manifold assembly and/or reduce a cost of the manifold assembly. For example, the intake passage, return passage, intake nozzles, and return nozzles may be each formed with a same wall thickness, such as the smaller, second thickness (e.g., 1.5 millimeters), via the additive manufacturing process.

Figure 8:
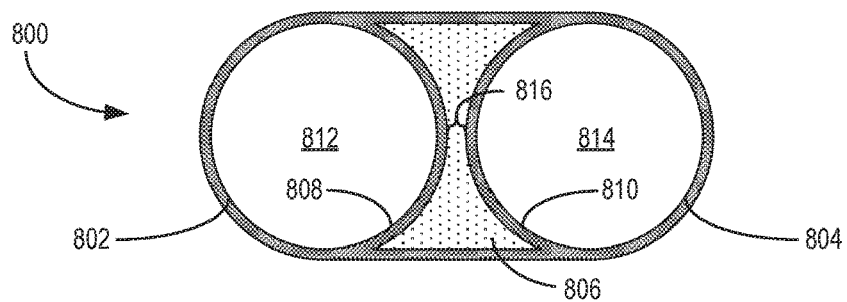
FIGS. 8-21 show cross-sectional views of various sections for cooling manifolds of PET/CT imaging systems, the sections formed by an additive manufacturing process.
Figure 9:
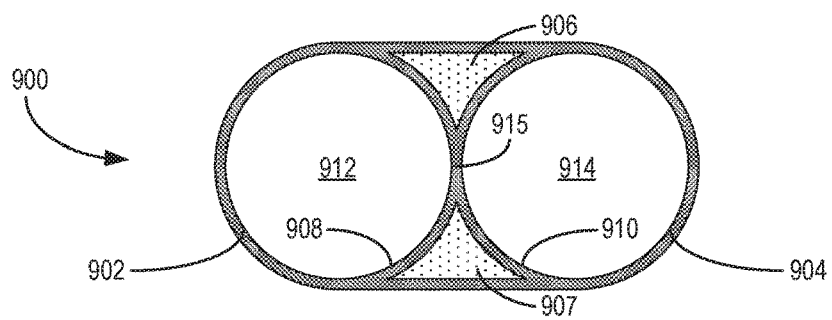
Figure 10:
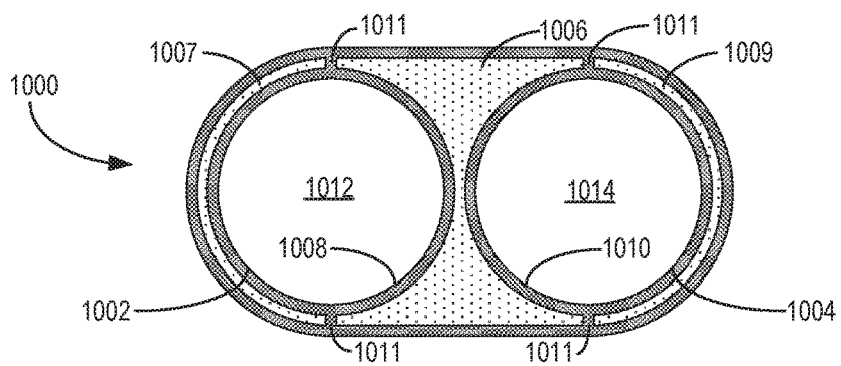
Figure 11:
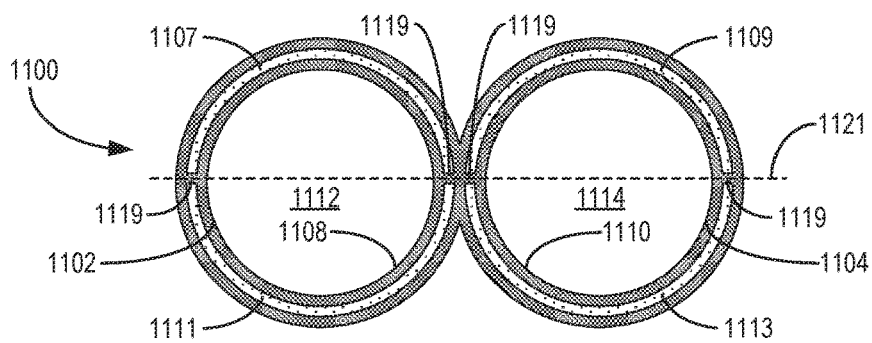
Figure 12:
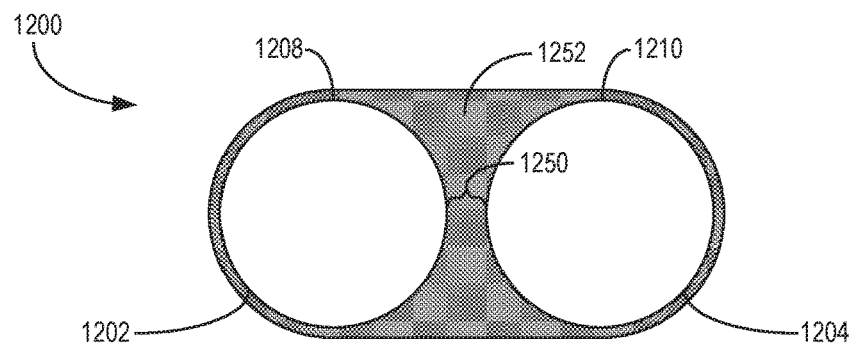
Figure 13:
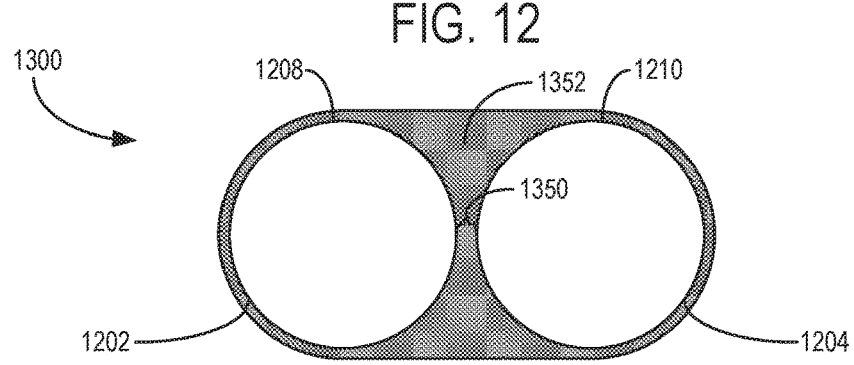
Figure 14:
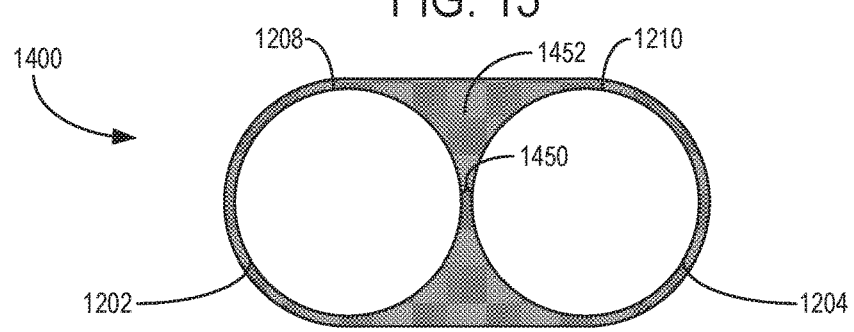
Figure 15:
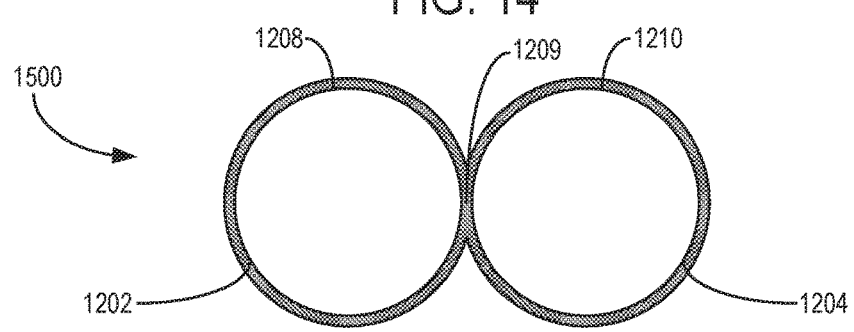
Figure 16:
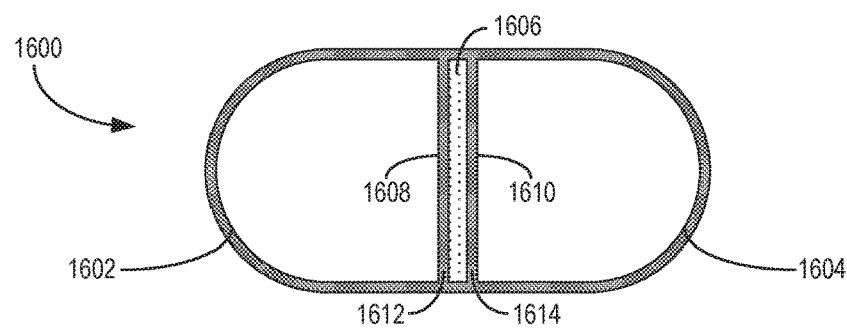
Figure 17:
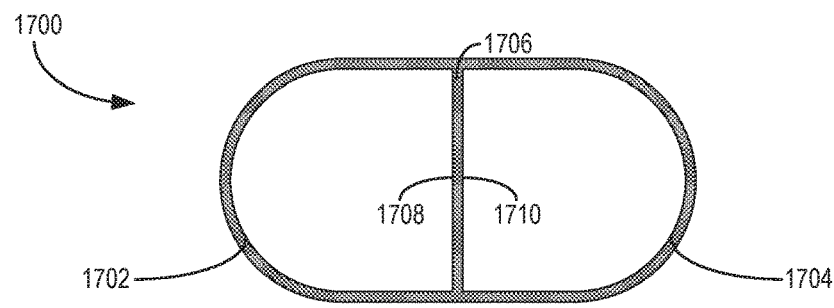
Figure 18:
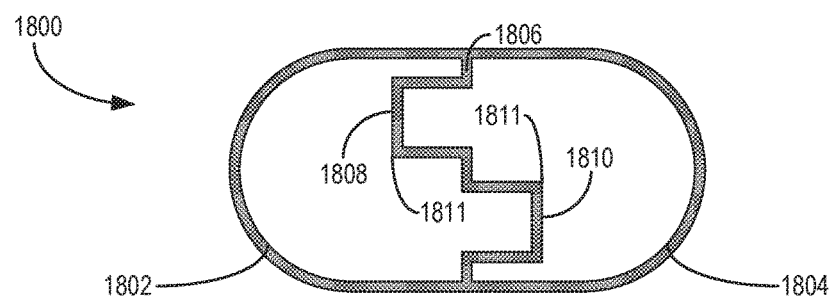
Figure 19:
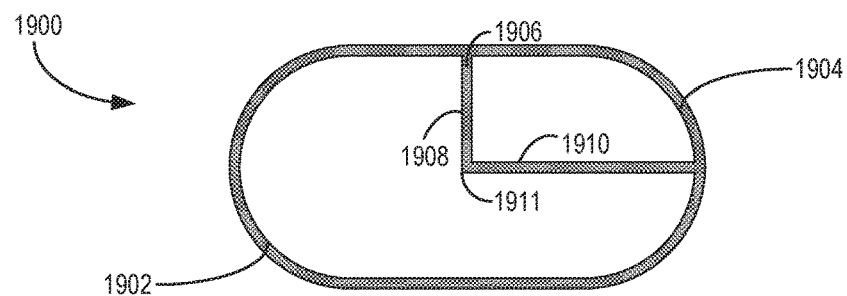
Figure 20:
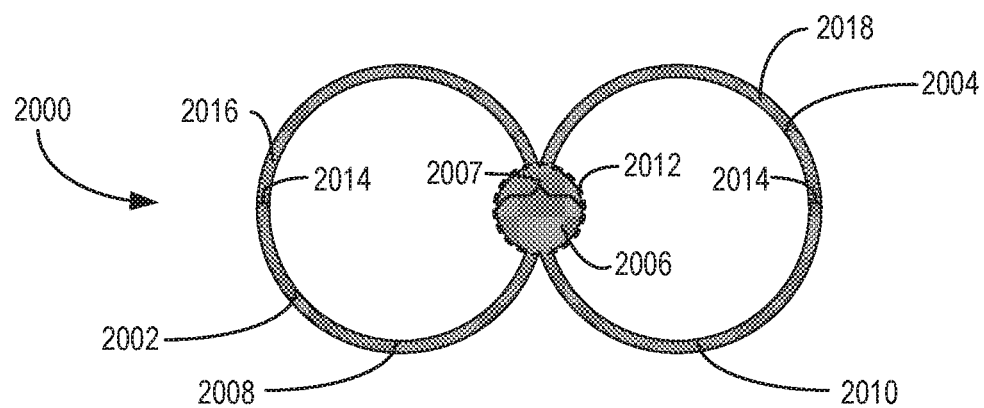
Figure 21:
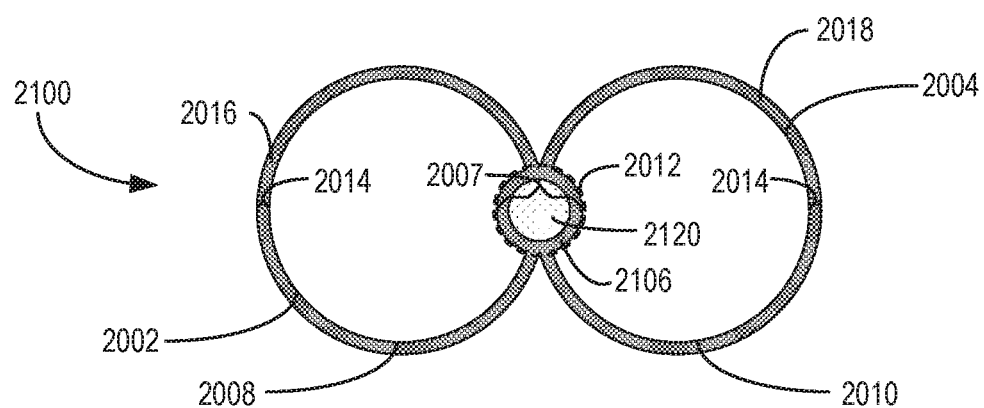

FIG. 8 shows a cross-sectional view of section 800, FIG. 9 shows a cross-sectional view of section 900, FIG. 10 shows a cross-sectional view of section 1000, and FIG. 11 shows a cross-sectional view of section 1100, with each of the sections 800, 900, 1000, and 1100 including at least one reservoir configured to reduce an amount of thermal energy transferred between passages of the sections. FIG. 12 shows a cross-sectional view of section 1200, FIG. 13 shows a cross-sectional view of section 1300, FIG. 14 shows a cross-sectional view of section 1400, and FIG. 15 shows a cross-sectional view of section 1500, with each of the sections 1200, 1300, 1400, and 1500 including different thicknesses of material surrounding the intake passage and return passage of each section. FIG. 16 shows a cross-sectional view of section 1600, FIG. 17 shows a cross-sectional view of section 1700, FIG. 18 shows a cross-sectional view of section 1800, and FIG. 19 shows a cross-sectional view of section 1900, with each of the sections 1600, 1700, 1800, and 1900 including different wall configurations separating the intake passage and return passage of each section. FIG. 20 shows a cross-sectional view of section 2000, and FIG. 21 shows a cross-sectional view of section 2100, with sections 2000 and 2100 including rounded walls separating the intake passage and return passage of each section. Throughout FIGS. 8-21, similar parts may be labeled similarly and not re-introduced.

In some examples, one or more of the sections described with reference to FIGS. 8-21 may be included within the manifold assemblies described above (e.g., manifold assembly 204 shown by FIGS. 2-3, manifold assembly 400 shown by FIG. 4, manifold assembly 600 shown by FIG. 6, and/or manifold assembly 700 shown by FIG. 7). For example, first section 404 of manifold assembly 400 may be similar to section 800 shown by FIG. 8, third section 606 of manifold assembly 600 may be similar to section 900 shown by FIG. 9, etc. Other examples are possible.

Further, in some examples, the manifold assemblies described above may include two or more sections similar to those shown by FIGS. 8-11, with at least two of the sections being different relative to each other. For example, first section 404 of manifold assembly 400 may include a cross-section similar to that of section 800 shown by FIG. 8, and third section 408 of manifold assembly 400 may include a cross-section similar to that of section 1000 shown by FIG. 10. Other examples are possible.

FIG. 8 shows section 800. The section 800 includes an intake passage 802 and return passage 804 (e.g., similar to the intake passages and return passages described above, such as intake passage 504 and return passage 502 of section 500). Intake passage 802 includes an inner surface 808 forming an interior 812 of the intake passage 802 (e.g., encircling the interior 812), and return passage 804 includes an inner surface 810 forming an interior 814 of the return passage 804 (e.g., encircling the interior 814).

The interior 812 of the intake passage 802 is fluidly isolated from the interior 814 of the return passage 804, such that fluid (e.g., coolant) does not flow directly from the intake passage 802 to the return passage 804 (or vice versa), and the inner surface 808 of the intake passage 802 does not contact (e.g., touch) the inner surface 810 of the return passage 804. The inner surface 808 is separated from the inner surface 810 by a width 816 of the section 800, with a reservoir 806 disposed between the inner surface 808 and inner surface 810.

Reservoir 806 may be adapted to reduce an amount of heat transferred from the interior 814 of the return passage 804 to the interior 812 of the intake passage 802 (or vice versa). For example, reservoir 806 may include a material (e.g., insulating foam) having a relatively low thermal conductivity disposed therein, with the material reducing the heat transferred between the intake passage 802 and the return passage 804. In one example, the reservoir 806 may be a vacuum reservoir, with the material disposed therein being a gas (e.g., air) having a very low pressure relative to atmospheric pressure (e.g., $10^{-6}$ atm). In other examples, the reservoir 806 may include a different type of insulating material. By positioning the inner surface 808 and inner surface 810 away from each other by the width 816 (e.g., across from each other, at opposite sides of the reservoir 806), the amount of heat transferred from the interior 814 of the return passage 804 to the interior 812 of the intake passage 802 (or vice versa) may be reduced.

In some examples, reservoir 806 may be sealed at opposing ends of the section 800 (e.g., opposing ends similar to first end 460 and second end 478 of each section of the manifold assembly 400 shown by FIG. 4). For example, reservoir 806 may be sealed by one or more walls of the section 800 positioned at the opposing ends, such that material within the reservoir 806 does not come into contact with fluids disposed within the intake passage 802 and return passage 804. In other examples, the material disposed within the reservoir 806 may seal the reservoir 806 from the intake passage 802 and return passage 804. For example, the reservoir 806 may be filled with an insulating material (e.g., foam or rubber), and the insulating material may block fluids from flowing into the reservoir 806 from the intake passage 802 and/or return passage 804.

Forming the section 800 via the additive manufacturing process enables the reservoir 806 to have a larger variety of configurations. For example, as the intake passage 802, return passage 804, and reservoir 806 are being formed via the additive manufacturing process, the reservoir 806 may be filled with the insulating material in order to reduce a number of steps to manufacture the section 800. In other examples, the reservoir 806 may be filled with the insulating material following formation of the intake passage 802, return passage 804, and reservoir 806 via the additive manufacturing process. For example, foam may be injected into the reservoir 806 from one or more ends of the section 800 after the section 800 is fully formed via the additive manufacturing process.

FIG. 9 shows section 900. Section 900 includes some elements similar to section 800. For example, section 900 includes intake passage 902 having inner surface 908 and interior 912, similar to intake passage 802, inner surface 808, and interior 812 (respectively) of section 800. Additionally, section 900 includes return passage 904 having inner surface 910 and interior 914, similar to return passage 804, inner surface 810, and interior 814 (respectively) of section 800. However, instead of including a single reservoir similar to the example of reservoir 806, section 900 includes two opposing reservoirs 906 and 907. The reservoirs 906 and 907 are separated from each other by wall 915, with the wall 915 being formed by both of the inner surface 908 of the intake passage 902 and the inner surface 910 of the return passage 904.

In some examples, the reservoirs 906 and 907 may be separated from each other along an entire length of the section 900 (e.g., from a first end of the section 900 to a second end of the section 900, with the first and second ends being similar to first end 460 and second end 478 of the sections of manifold assembly 400 shown by FIG. 4). In other examples, the reservoirs 906 and 907 may be joined to each other at one or more locations along the length of the section 900.

Each of the reservoirs may include a material similar to the material included by the reservoir 806 of section 800, in some examples. In other examples, one of the reservoirs (e.g., reservoir 906 or reservoir 907) may include a different material relative to the other reservoir. For example, reservoir 906 may be configured as a vacuum reservoir as described above with reference to reservoir 806, and reservoir 907 may include an insulating material (e.g., rubber, foam, etc.). In each example, manufacturing the section 900 via the additive manufacturing process enables the reservoirs 906 and 907 to be included more easily within the section 900. For example, the reservoirs 906 and 907 (and/or the other reservoirs described herein) may be shaped such that the reservoirs are not easily formed by non-additive manufacturing processes (e.g., molding). The shapes of the reservoirs may include undercuts or other features that are often difficult and/or expensive to produce via non-additive manufacturing processes. By forming the reservoirs 906 and 907 (and the other reservoirs described herein) via the additive manufacturing process, the shapes of the reservoirs may be produced with a wider range of complex features (e.g., undercuts) and/or with a reduced cost.

FIG. 10 shows section 1000, with section 1000 including several elements similar to those shown by FIGS. 8-9 and described above with reference to section 800 and section 900. For example, section 1000 includes intake passage 1002 having inner surface 1008 and interior 1012 (e.g., similar to intake passage 802, inner surface 808, and interior 812 of section 800, and/or intake passage 902, inner surface 908, and interior 912 of section 900), return passage 1004 having inner surface 1010 and interior 1014 (e.g., similar to return passage 804, inner surface 810, and interior 814 of section 800, and/or return passage 904, inner surface 910, and interior 914 of section 900), and reservoir 1006 disposed between the inner surface 1008 and the inner surface 1010 (e.g., similar to reservoir 806 and/or reservoirs 906 and 907, in some aspects).

Section 1000 further includes a second reservoir 1007 positioned to surround a portion of the intake passage 1002, and a third reservoir 1009 positioned to surround a portion of the return passage 1004. Each of the reservoirs 1006, 1007, and 1009 may be separated from each other by a plurality of walls 1011. In other examples, one or more of the reservoirs 1006, 1007, and 1009 may be joined to each other at one or more locations along the section 1000 (e.g., along a length of the section 1000, between opposing ends of the section 1000 similar to the examples described above). In the configuration shown by FIG. 10, the reservoir 1006 may have an increased volume relative to a volume of the reservoir 1007 and/or relative to a volume of the reservoir 1009. The increased volume of the reservoir 1006 may further reduce an amount of heat transferred between the intake passage 1002 and return passage 1004, while the reservoirs 1007 and 1009 may reduce a heat exchange of the intake passage 1002 and return passage 1004 (respectively) with atmospheric air surrounding the section 1000. Similar to the examples described above, one or more of the reservoirs 1006, 1007, and 1009 may be a vacuum reservoir including a gas stored at a pressure lower than atmospheric pressure, or one or more of the reservoirs may include a different thermally insulating material (e.g., rubber, foam, etc.). Further, one or more of the reservoirs 1006, 1007, and 1009 may be configured differently than each other reservoir. For example, reservoir 1006 may be configured as a vacuum reservoir, and reservoirs 1007 and 1009 may include the different thermally insulating material (e.g., rubber, foam, etc.). By manufacturing the section 1000 via the additive manufacturing process, an increased variety of configurations (e.g., combinations) of the reservoirs may be possible.

FIG. 11 shows another section 1100 including several components similar to the sections described above with reference to FIGS. 8-11. For example, section 1100 includes intake passage 1102 having inner surface 1108 and interior 1112 (similar to intake passage 802, inner surface 808, and interior 812, in one example), return passage 1104 having inner surface 1110 and interior 1114 (similar to return passage 804, inner surface 810, and interior 814, in one example), and a plurality of reservoirs, described below.

The section 1100 includes a first reservoir 1107, a second reservoir 1109, a third reservoir 1111, and a fourth reservoir 1113. In the example shown by FIG. 11, each of the reservoirs are separated from each other by walls 1119, with each of the walls 1119 positioned along a same plane (as indicated by axis 1121). In other examples, the walls 1119 may not be positioned along the same plane (e.g., one or more of the walls 1119 may be positioned along a different plane relative to one or more other walls 1119). Similar to the examples described above, one or more of the reservoirs may be configured as a vacuum reservoir including a gas stored at a relatively low pressure (e.g., relative to atmospheric pressure), and/or one or more of the reservoirs may include a different insulating material (e.g., rubber, foam, etc.). Forming the section 1100 via the additive manufacturing process may enable each reservoir (e.g., reservoirs 1107, 1109, 1111, and 1113) to be configured individually relative to each other reservoir.

FIGS. 12-15 each show cross-sectional views of sections including an intake passage 1202 and a return passage 1204. Intake passage 1202 may be similar to the intake passages described above (e.g., intake passage 802, intake passage 902, etc.), and return passage 1204 may be similar to the return passages described above (e.g., return passage 804, return passage 904, etc.).

FIG. 12 shows section 1200 including a buffer portion 1252. Buffer portion 1252 may be formed of a same material as the intake passage 1202 and return passage 1204. For example, the buffer portion 1252, intake passage 1202, and return passage 1204 may each be formed of a metal material (e.g., stainless steel) via the additive manufacturing process. The buffer portion 1252 extends between the intake passage 1202 and return passage 1204 and partially surrounds each of the intake passage 1202 and return passage 1204. The intake passage 1202 includes an inner surface 1208 and the return passage 1204 includes an inner surface 1210, with the inner surface 1208 and inner surface 1210 being separated from each other by a width 1250 of the buffer portion 1252. The buffer portion 1252 may reduce an amount of heat transferred between the intake passage 1202 and the return passage 1204, and/or may increase a strength (e.g., rigidity) of the section 1200.

FIG. 13 shows section 1300 including several components similar to the section 1200 (e.g., intake passage 1202, return passage 1204, etc.). However, section 1300 includes a buffer portion 1352 having a different width 1350 (e.g., smaller width) relative to the width 1250 of buffer portion 1252 of section 1200. In some examples, reducing the width of the buffer portion may decrease a cost and/or manufacturing time of the section 1300 relative to sections that have wider buffer portions (e.g., section 1200). Further FIG. 14 shows section 1400 having a buffer portion 1452 with a width 1450 less than the width 1350 of buffer portion 1352 of section 1300. FIG. 15 shows section 1500 including intake passage 1202 and return passage 1204 separated only by wall 1209. In the example of section 1500, the intake passage 1202 and return passage 1204 are not surrounded by a buffer portion. As a result, a weight, cost, and/or production time of the section 1500 may be reduced.

FIGS. 16-19 each show different examples of sections that include an intake passage and return passage separated by one or more walls having various shapes and/or sizes. For example, FIG. 16 shows section 1600 including intake passage 1602 and return passage 1604 separated by walls 1612 and 1614. Wall 1612 is formed partly by inner surface 1608 of intake passage 1602, and wall 1614 is formed partly by inner surface 1610 of return passage 1604. The walls 1612 and 1614 may be flat, planar walls (e.g., without curvature), in some examples, and other portions of the intake passage 1602 and/or return passage 1604 may include curved surfaces.

Section 1600 includes a reservoir 1606 positioned between the walls 1612 and 1614. The reservoir 1606 may have a configuration similar to the reservoirs described above with reference to FIGS. 8-11 (e.g., reservoir 1606 may be a vacuum reservoir including a gas having a relatively low pressure, and/or may include a different insulating material).

FIG. 17 shows section 1700 including several components similar to section 1600 of FIG. 16. Section 1700 includes intake passage 1702 and return passage 1704, with intake passage 1702 separated from return passage 1704 by wall 1706. Inner surface 1708 of intake passage 1702 forms one side of the wall 1706, and inner surface 1710 of return passage 1704 forms an opposing, second side of the wall 1706. The intake passage 1702 and return passage 1704 are separated only by the wall 1706, and in some examples the wall 1706 may be a flat, planar wall (e.g., without curvature). Section 1700 does not include a reservoir similar to reservoir 1606 of section 1600.

FIG. 18 shows section 1800 including intake passage 1802 having inner surface 1808 and return passage 1804 having inner surface 1810. The inner surface 1808 forms a first surface of wall 1806 separating the intake passage 1802 from the return passage 1804, and inner surface 1810 forms an opposing, second surface of the wall 1806. In the example shown by FIG. 18, the wall 1806 is not a flat, planar wall. Instead, wall 1806 includes a plurality of corners 1811. In some examples, such as the example shown by FIG. 18, the corners 1811 may be right-angled corners. In other examples, corners 1811 may be curved or angled by a different amount. Further, other examples may include a different number of corners 1811 relative to the example shown by FIG. 18. The additive manufacturing process enables the wall 1806 to be produced with a wide variety of different shapes (e.g., different number, arrangement, and/or shape of corners 1811). In some examples, the shape of wall 1806 may be based on a desired flow characteristic of fluid (e.g., coolant) flowing through the intake passage 1802 and/or return passage 1804. For example, the wall 1806 may be shaped (e.g., produced) via the additive manufacturing process along with the intake passage 1802 and return passage 1804 in order to achieve a desired flow rate, flow direction, flow turbulence, etc. of fluid through the intake passage 1802 and/or return passage 1804.

FIG. 19 shows section 1900 including intake passage 1902 having inner surface 1908 and return passage 1904 having inner surface 1910. The intake passage 1902 and return passage 1904 are separated by wall 1906. Wall 1906 includes a single corner 1911, and the corner 1911 is positioned such that a volume of the intake passage 1902 is larger than a volume of the return passage 1904. In this configuration, a flow speed and/or pressure of fluid (e.g., coolant) within the return passage 1904 may be greater than a flow speed and/or pressure of fluid within the intake passage 1902. In other examples, the corner 1911 may be angled differently such that the volume of the return passage 1904 is greater than the volume of the intake passage 1902. In such configurations, the flow speed and/or pressure of fluid within the intake passage 1902 may be greater than the flow speed and/or pressure of fluid within the return passage 1904. In yet other configurations, the angle of the corner 1911 may vary along an entire length of the section 1900, such that in some locations of the section 1900 the volume of the intake passage 1902 is greater than the volume of the return passage 1904, and in other locations of the section 1900 the volume of the intake passage 1902 is less than the volume of the return passage 1904. By forming the wall 1906 via the additive manufacturing process, the flow speed and/or pressure of fluid may be altered at some locations of the section 1900 relative to other locations of the section 1900 (e.g., in order to adjust flow rates to certain intake nozzles and/or return nozzles of the section 1900).

FIG. 20 shows section 2000 including intake passage 2002 having inner surface 2008 and return passage 2004 having inner surface 2010. Section 2000 further includes buffer portion 2006 positioned between the intake passage 2002 and return passage 2004, with buffer portion 2006 being formed by each of the inner surface 2008 and the inner surface 2010. In the example shown by FIG. 20, the buffer portion 2006 is a solid portion of the section 2000 and may be formed from a same material as the intake passage 2002 and return passage 2004 via the additive manufacturing process. The buffer portion 2006 may have a circular cross-section, as indicated by dashed line 2012, and a thickness 2007 (e.g., width or diameter) of the buffer portion 2006 may be greater than a thickness 2014 of walls 2016 and 2018 forming the intake passage 2002 and return passage 2004, respectively. The increased thickness of the buffer portion 2006 relative to the walls 2016 and 2018 may reduce an amount of heat transferred from the return passage 2004 to the intake passage 2002 (or vice versa). As a result, heating of fluid (e.g., coolant) flowing through the intake passage 2002 by the return passage 2004 due to the proximity of the intake passage 2002 to the return passage 2004 may be reduced, and the fluid may flow to components of the imaging system (e.g., cold plates 56 described above with reference to FIG. 3) at a lower temperature. The lower temperature of the fluid may result in a more efficient cooling of the components of the imaging system.

FIG. 21 shows section 2100 including several components similar to section 2000 described above. For example, section 2100 includes intake passage 2002 having wall 2016 and inner surface 2008, and return passage 2004 having wall 2018 and inner surface 2010. The wall 2016 and 2018 have thickness 2014, as described above. However, section 2100 includes buffer portion 2106 having a reservoir 2120 disposed therein. In some examples, reservoir 2120 may be configured similar to the reservoirs described above with reference to FIGS. 8-11 and FIG. 16. For example, reservoir 2120 may be configured as a vacuum reservoir and may include a gas having a relatively low pressure stored therein (e.g., lower than atmospheric pressure), and/or may include a different material having a low thermal conductivity (e.g., relative to a material forming the walls 2016 and 2018). Reservoir 2120 may be formed along with the walls 2016 and 2018 via the additive manufacturing process in order to further reduce an amount of heat transferred from the return passage 2004 to the intake passage 2002 (or vice versa) during conditions in which fluid (e.g., coolant) flows through the intake passage 2002 to components of the imaging system, and flows from the components of the imaging system through return passage 2004 (e.g., as described above with reference to manifold assembly 204, manifold assembly 400, etc.).

Figure 22:
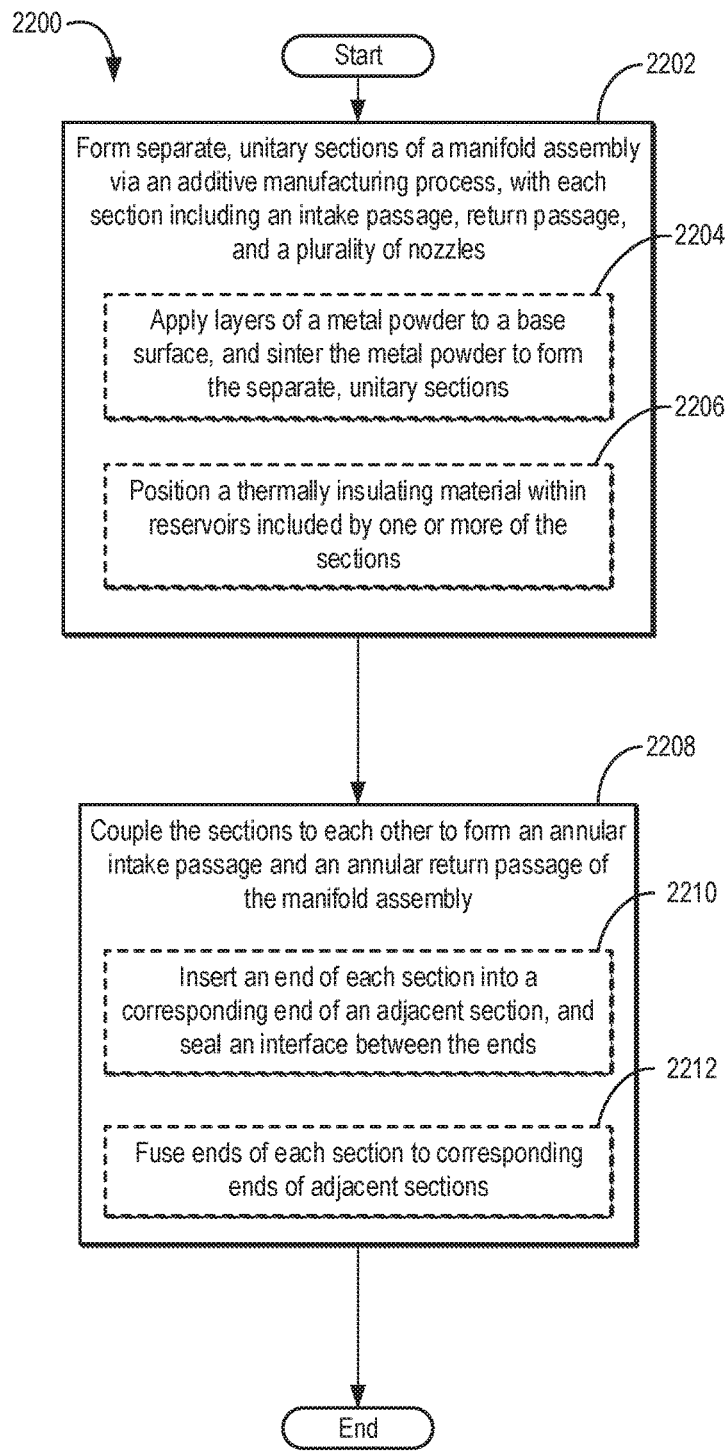
FIG. 22 shows a flow chart illustrating a method for producing a manifold assembly for a cooling system of a PET/CT imaging system, the manifold assembly having a plurality of unitary sections formed by an additive manufacturing process.

Turning now to FIG. 22, a flowchart is shown illustrating a method 2200 for producing a manifold assembly for a cooling system of a PET/CT imaging system. In some examples, the manifold assembly referenced by method 2200 may be similar to manifold assembly 400 shown by FIG. 4 and described above, manifold assembly 600 shown by FIG. 6 and described above, manifold assembly 700 shown by FIG. 7 and described above, etc.

The method at 2202 includes forming separate, unitary sections of a manifold assembly via an additive manufacturing process (e.g., 3D printing, an example of which is described below), with each section including an intake passage, return passage, and a plurality of nozzles. For example, the separate, unitary sections formed at 2202 may be similar to sections 404, 406, 408, 410, and 412 of manifold assembly 400, section 500 shown by FIG. 5, sections 602, 604, 606, 608, and 610 of manifold assembly 600, sections 701, 703, and 705 of manifold assembly 700, and/or the sections described above with reference to FIGS. 8-21 (e.g., sections 800, 900, 1000, 1100, 1200, 1300, 1400, 1500, 1600, 1700, 1800, 1900, 2000, and/or 2100). Each section includes a separate intake passage and return passage (e.g., similar to intake passage 504 and return passage 502 of section 500 described above with reference to FIG. 5).

In one example, one or more of the sections formed at 2202 may be different relative to each other section formed at 2202. For example, one or more of the sections may include a different number, spacing, and/or angle of nozzles (e.g., intake nozzles and return nozzles, similar to intake nozzles 422 and return nozzles 424 of manifold assembly 400, intake nozzles 514 and return nozzles 512 of section 500, intake nozzles 626 and return nozzles 628 of manifold assembly 600, etc.) relative to one or more of the other sections (e.g., similar to the example of intake nozzles 620, 624, 630, and 634, and return nozzles 622, 618, 632, and 636 described above with reference to manifold assembly 600 of FIG. 6). Further, one or more of the sections formed at 2202 may include a different intake passage and/or return passage shape, size, and/or position relative to one or more of the other sections. For example, one of the sections formed at 2202 may include a configuration similar to section 1700 shown by FIG. 17, and one or more of the sections formed at 2202 may include a configuration similar to the section 1900 shown by FIG. 19.

In addition to the intake passage, return passage, and nozzles formed with the sections at 2202, one or more of the sections may include one or more components such as brackets (e.g., brackets 418), intake inlets (e.g., intake inlet 414), return outlets (e.g., return outlet 416), and/or drain outlets (e.g., drain outlet 426) formed integrally with the sections via the additive manufacturing process. Specifically, the one or more components are formed together with their corresponding sections via the additive manufacturing process such that the components are not fused, welded, or otherwise coupled to the sections after the sections are formed. Instead, the components are formed together with the sections, such that the intake passage, return passage, nozzles, brackets, and other components of the sections are comprised of a same, continuous material. For example, intake passage 504, return passage 502, wall 510, intake nozzles 514, return nozzles 512, brackets 516, and arms 520 shown by FIG. 5 are formed as a single, unitary piece (e.g., section 500) via the additive manufacturing process according to the method at 2202.

In some examples, the additive manufacturing process of the method at 2202 includes applying layers of a metal powder to a base surface, and sintering the metal powder to form the separate, unitary sections, as indicated at step 2204. For example, the base surface may be a table or working area of an additive manufacturing machine (e.g., a 3D printer), and the metal powder may comprise a desired material of the sections of the manifold assembly (e.g., stainless steel). In some examples, the metal powder may include one or more polymeric binders adapted to reduce a sintering temperature of the metal powder and/or increase a strength of sections formed by the metal powder. Sintering the metal powder may include energizing a laser to selectively heat portions of each layer of the metal powder in order to melt the metal powder and form a desired shape (e.g., a shape of each section). For example, the laser may be energized in order to sinter a single layer of the metal powder to form a portion of each of the intake passage, return passage, and one or more intake nozzles and return nozzles of a single section of the manifold assembly.

Turning momentarily to FIGS. 23-25, various steps in an additive manufacturing process similar to the process described above at step 2204 of method 2202 are shown. Specifically, FIGS. 23-25 show forming a section 2300 of a manifold assembly via the additive manufacturing process, similar to the sections described above (e.g., fourth section 608 of manifold assembly 600 of FIG. 6). FIG. 23 shows the section 2300 during a first step (e.g., stage) of manufacturing, FIG. 24 shows the section 2300 during a second step of manufacturing, and FIG. 25 shows the completed section 2300 (e.g., after the first and second steps).

With regard to FIG. 23, section 2300 is shown partially formed on base surface 2304 (e.g., similar to the base surface described above at 2204), with the base surface supporting metal powder 2302 (e.g., similar to the metal powder described above at 2204). At the step illustrated by FIG. 23, several layers of the metal powder 2302 have been sintered (e.g., laser sintered, as described above at 2204) in order to partially form return passage 2306 of the section 2300.

FIG. 24 shows a step following the step illustrated by FIG. 23. Between the steps illustrated by FIG. 23 and FIG. 24, several additional layers of the metal powder 2302 have been sintered in order to build up (e.g., form) the shape of the section 2300. At the step illustrated by FIG. 24, the section 2300 includes a plurality of intake nozzles 2400 and return nozzles 2402 (e.g., similar to intake nozzles 626 and return nozzles 628 of the sections of manifold assembly 600 of FIG. 6), with some intake nozzles 2400, return nozzles 2402, and brackets 2404 (e.g., similar to brackets 616 of FIG. 6) being in a partially formed condition as indicated by arrows 2420. FIG. 24 illustrates that the intake nozzles 2400, return nozzles 2402, and brackets 2404 are not separate components that are welded or otherwise coupled to the section 2300. Instead, the intake nozzles 2400, return nozzles 2402, brackets 2404, return passage 2306, and intake passage (not shown) are all formed together as a unitary piece (e.g., formed together as section 2300) via the additive manufacturing process (e.g., via sintering of layers of the metal powder 2302), such that during various stages of the manufacturing process (e.g., the step shown by FIG. 24), the intake nozzles 2400, return nozzles 2402, brackets 2404, return passage 2306, and intake passage may each be in a partially formed condition within the same, unitary piece. FIG. 25 shows the section 2300 in a fully formed condition, with the metal powder 2302 removed from the base surface 2304.

Returning now to FIG. 22, in some examples, step 2202 may include positioning a thermally insulating material within reservoirs included by one or more of the sections, as indicated at step 2206. For example, as described above with reference to the sections shown by FIGS. 8-11 and FIG. 16, one or more of the sections may include one or more reservoirs (e.g., reservoir 806 of section 800 of FIG. 8, reservoirs 906 and 907 of section 900 of FIG. 9, etc.). In one example, at step 2202, gases (e.g., air) within the one or more reservoirs may be removed (e.g., vacuumed) from the reservoirs and the reservoirs may be sealed in order to thermally insulate the intake passage from the return passage of the sections including the reservoirs. For example, because the pressure of gases remaining within the reservoirs may be much lower than atmospheric pressure, the gases may function as an insulating material. In another example, at step 2202, a different insulating material (e.g., foam) may be inserted into the reservoirs (e.g., pumped into the reservoirs) in order to reduce an amount of heat transferred between the intake passage and return passage of each section including the reservoirs. In yet another example, one or more of the sections may include a plurality of reservoirs (e.g., similar to section 1000 shown by FIG. 10), with one or more of the reservoirs being vacuumed and sealed, and with one or more of the reservoirs having the different insulating material inserted therein.

The method continues from 2202 to 2208 where the method includes coupling the sections to each other to form an annular intake passage and an annular return passage of the manifold assembly. For example, as described above, each of the sections includes an intake passage and a return passage. During conditions in which the sections are coupled together, the intake passages of the sections are fluidly coupled together to form the annular intake passage, and the return passages of the sections are fluidly coupled together to form the annular return passage (e.g., similar to the annular intake passages and annular return passages described above with reference to manifold assemblies 400, 600, and 700).

In some examples, step 2208 may include inserting an end of each section into a corresponding end of an adjacent section, and sealing an interface between the ends, as indicated at step 2210. For example, with regard to the manifold assembly 600 shown by FIG. 6, at 2210 the second end 638 of first section 602 may be inserted into the first end 640 of the second section 604, the second end 638 of the fifth section 610 may be inserted into the first end 640 of the first section 602, etc., in order to couple the sections together to form the manifold assembly. Sealing the interface between the ends (e.g., the interface between the second end 638 of the first section 602 and the first end 640 of the second section 604) may include positioning one or more gaskets within the interface and/or coupling the ends together via one or more fasteners (e.g., grommets).

Further, in some examples, step 2208 may include fusing ends of each section to corresponding ends of adjacent sections, as indicated at step 2212. Fusing the ends may occur alternately from, or in addition to, coupling the ends of the sections together at step 2210. In one example, after inserting the second end 638 of first section 602 of manifold assembly 600 into the first end 640 of the second section 604, the second end 638 of the first section 602 may be fused (e.g., welded) to the first end 640 of the second section 604. In other examples, the ends may be fused without inserting the ends of sections into the corresponding ends. For example, first end 460 of first section 404 shown by FIG. 4 may be fused (e.g., welded) to second end 462 of second section 406 without inserting the first end 460 into the second end 462 (or vice versa), as indicated by joint 450 of FIG. 4.

By forming the sections of the manifold assembly as separate, unitary pieces, and coupling the ends of the sections together in order to form both of the intake manifold having the annular intake passage and the return manifold having the annular return passage, a number of components and/or welds utilized to form the manifold assembly may be reduced. For example, forming the intake nozzles, return nozzles, and brackets with each section via the additive manufacturing process enables the intake nozzles, return nozzles, and brackets to be included by the manifold assembly without individually welding the intake nozzles, return nozzles, and brackets to the sections. Further, because the ends of adjacent sections of the manifold assembly are joined together, sections may be individually removed from the manifold assembly for maintenance, repair, and/or replacement without replacing the entire manifold assembly and without altering the relative arrangement (e.g., relative angle, spacing, etc.) of the intake nozzles, return nozzles, etc. Additionally, because the intake nozzles, return nozzles, brackets, and inlets and outlets of the sections are not separate pieces that are welded to the sections, a thickness of the walls of the intake passage, return passage, intake nozzles, return nozzles, and brackets of each section may be reduced, decreasing an amount of material consumed in manufacturing the manifold assembly and a cost of the manifold assembly. Further, a manufacturing time of the manifold assembly may be decreased.

A technical effect of the disclosure is to provide a manifold assembly for a PET system that does not include welded nozzles or welded mounting brackets in order to reduce a cost and/or manufacturing time of the manifold assembly. Another technical effect of the disclosure is to provide a manifold assembly for a PET system having unitary sections formed via an additive manufacturing process in order to reduce a thickness of walls of the manifold assembly and increase desirable flow characteristics of fluid disposed within the manifold assembly.

In one embodiment, a manifold assembly for an imaging system comprises: an intake manifold and a return manifold formed by a plurality of unitary sections, the intake manifold and return manifold positioned adjacent to each other and separated by a shared wall; and a plurality of nozzles, with each nozzle of the plurality of nozzles formed by a corresponding section of the plurality of unitary sections. In a first example of the manifold assembly, the manifold assembly further includes wherein the intake manifold and return manifold are each centered on a same, central axis of the manifold assembly, with the intake manifold, return manifold, and shared wall encircling the central axis. A second example of the manifold assembly optionally includes the first example, and further includes wherein the intake manifold includes an annular intake passage formed by a plurality of arcuate intake passages, the return manifold includes an annular return passage formed by a plurality of arcuate return passages, and the shared wall comprises a plurality of arcuate walls. A third example of the manifold assembly optionally includes one or both of the first and second examples, and further includes wherein each arcuate intake passage of the plurality of arcuate intake passages, each arcuate return passage of the plurality of arcuate return passages, and each arcuate wall of the plurality of arcuate walls is formed by a corresponding section of the plurality of unitary sections. A fourth example of the manifold assembly optionally includes one or more or each of the first through third examples, and further includes wherein one or more arcuate walls of the plurality of arcuate walls forms a reservoir having a thermally insulating material disposed therein, the thermally insulating material having a lower thermal conductivity than a material of the one or more arcuate walls. A fifth example of the manifold assembly optionally includes one or more or each of the first through fourth examples, and further includes wherein each section of the plurality of unitary sections includes exactly one arcuate intake passage of the plurality of arcuate intake passages and exactly one arcuate return passage of the plurality of arcuate return passages. A sixth example of the manifold assembly optionally includes one or more or each of the first through fifth examples, and further includes wherein each section of the plurality of unitary sections includes an end coupled to a corresponding, adjacent section of the plurality of unitary sections. A seventh example of the manifold assembly optionally includes one or more or each of the first through sixth examples, and further includes wherein the shared wall fluidly isolates the annular intake passage from the annular return passage. An eighth example of the manifold assembly optionally includes one or more or each of the first through seventh examples, and further includes wherein the plurality of nozzles includes a plurality of intake nozzles and a plurality of return nozzles, the plurality of intake nozzles formed with the annular intake passage and in fluidic communication with the annular intake passage, and the plurality of return nozzles formed with the annular return passage and in fluidic communication with the annular return passage. A ninth example of the manifold assembly optionally includes one or more or each of the first through eighth examples, and further includes wherein the plurality of nozzles includes a plurality of nozzle sets, with each nozzle set of the plurality of nozzle sets including an intake nozzle and a return nozzle. A tenth example of the manifold assembly optionally includes one or more or each of the first through ninth examples, and further includes wherein each nozzle set of the plurality of nozzle sets is in fluidic communication with a corresponding detector assembly of a plurality of detector assemblies of the imaging system. An eleventh example of the manifold assembly optionally includes one or more or each of the first through tenth examples, and further includes wherein a first section of the plurality of unitary sections is integrally formed with a mounting bracket as a single piece, the mounting bracket adapted to couple the manifold assembly to the imaging system. A twelfth example of the manifold assembly optionally includes one or more or each of the first through eleventh examples, and further includes wherein a first section of the plurality of unitary sections is integrally formed with a drain outlet as a single piece, the drain outlet in fluidic communication with one of the intake manifold or the return manifold and adapted to flow coolant out of the manifold assembly via gravity. A thirteenth example of the manifold assembly optionally includes one or more or each of the first through twelfth examples, and further includes wherein the intake manifold includes an intake inlet and the return manifold includes a return outlet, the intake inlet and return outlet formed by one or more sections of the plurality of unitary sections.

In one embodiment, a method comprises: forming a plurality of separate, unitary sections of a manifold assembly for a positron emission tomography (PET) system via an additive manufacturing process, with each unitary section including an intake passage, return passage, a plurality of nozzles, and a shared wall separating the intake passage from the return passage; and coupling the plurality of unitary sections together to form an intake manifold and a return manifold of the manifold assembly. In a first example of the method, the method includes wherein coupling the plurality of sections together to form the intake manifold and return manifold includes only fitting an end of each section of the plurality of sections into a corresponding end of a corresponding, adjacent section of the plurality of adjacent sections. A second example of the method optionally includes the first example, and further includes wherein coupling the plurality of sections together to form the intake manifold and return manifold includes only fusing an end of each section of the plurality of sections with a corresponding end of a corresponding, adjacent section of the plurality of sections, and does not include any other fusing or coupling of any section of the plurality of sections to any other section of the plurality of sections. A third example of the method optionally includes one or both of the first and second examples, and further includes wherein the additive manufacturing process comprises 3D printing, and wherein forming the plurality of separate, unitary sections of the manifold assembly via the additive manufacturing process includes forming the intake passage, return passage, plurality of nozzles, and shared wall of each unitary section of the plurality of unitary sections entirely of a same material, and with the intake passage, return passage, and plurality of nozzles having a same wall thickness.

In one embodiment, a positron emission tomography (PET) system comprises: a plurality of photodetector assemblies positioned in an annular array encircling a bore of the PET system; and a manifold assembly including an annular coolant intake passage and an annular coolant return passage comprised of a plurality of unitary, arcuate sections, with each arcuate section of the plurality of arcuate sections formed integrally with a plurality of nozzles as a single piece via a 3D printing manufacturing process, the plurality of nozzles fluidly coupling the annular coolant intake passage and annular coolant return passage to the photodetector assemblies. In a first example of the PET system, the PET system includes wherein one or more arcuate section of the plurality of arcuate sections further comprises a mounting bracket or drain outlet formed integrally with the one or more arcuate section via the 3D printing manufacturing process, and wherein each arcuate section of the plurality of arcuate sections includes a wall separating the annular coolant intake passage from the annular coolant return passage and forming inner surfaces of each of the annular coolant intake passage and annular coolant return passage, the wall formed via the 3d printing manufacturing process.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A manifold assembly for an imaging system, comprising:
    an intake manifold and a return manifold formed by a plurality of unitary sections, the intake manifold and the return manifold positioned adjacent to each other and separated by a shared wall; and
    a plurality of nozzles, with each nozzle of the plurality of nozzles formed integrally with a corresponding section of the plurality of unitary sections,
    wherein a first section of the plurality of unitary sections is integrally formed with a drain outlet as a single piece, the drain outlet in fluidic communication with one of the intake manifold or the return manifold and adapted to flow coolant out of the manifold assembly via gravity.

2. The manifold assembly of claim 1, wherein the intake manifold and the return manifold are each centered on a same, central axis of the manifold assembly, with the intake manifold, the return manifold, and the shared wall encircling the central axis.

3. The manifold assembly of claim 1, wherein the intake manifold includes an annular intake passage formed by a plurality of arcuate intake passages, the return manifold includes an annular return passage formed by a plurality of arcuate return passages, and the shared wall comprises a plurality of arcuate walls.

4. The manifold assembly of claim 3, wherein each arcuate intake passage of the plurality of arcuate intake passages, each arcuate return passage of the plurality of arcuate return passages, and each arcuate wall of the plurality of arcuate walls is formed by a corresponding section of the plurality of unitary sections.

5. The manifold assembly of claim 4, wherein one or more arcuate walls of the plurality of arcuate walls forms a reservoir having a thermally insulating material disposed therein, the thermally insulating material having a lower thermal conductivity than a material of the one or more arcuate walls.

6. The manifold assembly of claim 4, wherein each section of the plurality of unitary sections includes exactly one arcuate intake passage of the plurality of arcuate intake passages and exactly one arcuate return passage of the plurality of arcuate return passages.

7. The manifold assembly of claim 3, wherein the shared wall fluidly isolates the annular intake passage from the annular return passage.

8. The manifold assembly of claim 3, wherein the plurality of nozzles includes a plurality of intake nozzles and a plurality of return nozzles, the plurality of intake nozzles formed with the annular intake passage and in fluidic communication with the annular intake passage, and the plurality of return nozzles formed with the annular return passage and in fluidic communication with the annular return passage.

9. The manifold assembly of claim 1, wherein each section of the plurality of unitary sections includes an end coupled to a corresponding, adjacent section of the plurality of unitary sections.

10. The manifold assembly of claim 1, wherein the plurality of nozzles includes a plurality of nozzle sets, with each nozzle set of the plurality of nozzle sets including an intake nozzle and a return nozzle.

11. The manifold assembly of claim 10, wherein each nozzle set of the plurality of nozzle sets is in fluidic communication with a corresponding detector assembly of a plurality of detector assemblies of the imaging system.

12. The manifold assembly of claim 1, wherein a first section of the plurality of unitary sections is integrally formed with a mounting bracket as a single piece, the mounting bracket adapted to couple the manifold assembly to the imaging system.

13. The manifold assembly of claim 1, wherein the intake manifold includes an intake inlet and the return manifold includes a return outlet, the intake inlet and the return outlet formed by one or more sections of the plurality of unitary sections.

14. A method, comprising:
forming a plurality of separate, unitary sections of a manifold assembly for a positron emission tomography (PET) system via an additive manufacturing process, with each unitary section including an intake passage, a return passage, a plurality of nozzles, and a shared wall separating the intake passage from the return passage; and
coupling the plurality of unitary sections together to form an intake manifold and a return manifold of the manifold assembly.

15. The method of claim 14, wherein coupling the plurality of unitary sections together to form the intake manifold and the return manifold includes only fitting an end of each section of the plurality of unitary sections into a corresponding end of a corresponding, adjacent section of the plurality of adjacent sections.

16. The method of claim 14, wherein coupling the plurality of unitary sections together to form the intake manifold and the return manifold includes only fusing an end of each section of the plurality of unitary sections with a corresponding end of a corresponding, adjacent section of the plurality of unitary sections, and does not include any other fusing or coupling of any section of the plurality of unitary sections to any other section of the plurality of unitary sections.

17. The method of claim 14, wherein the additive manufacturing process comprises 3D printing, and wherein forming the plurality of separate, unitary sections of the manifold assembly via the additive manufacturing process includes forming the intake passage, the return passage, the plurality of nozzles, and the shared wall of each unitary section of the plurality of unitary sections entirely of a same material, and with the intake passage, the return passage, and the plurality of nozzles having a same wall thickness.

18. A positron emission tomography (PET) system, comprising:
a plurality of photodetector assemblies positioned in an annular array encircling a bore of the PET system; and
a manifold assembly including an annular coolant intake passage and an annular coolant return passage comprised of a plurality of unitary, arcuate sections, with each arcuate section of the plurality of arcuate sections formed integrally with a plurality of nozzles as a single piece via a 3D printing manufacturing process, the plurality of nozzles fluidly coupling the annular coolant intake passage and the annular coolant return passage to the plurality of photodetector assemblies.

19. The PET system of claim 18, wherein one or more arcuate sections of the plurality of arcuate sections further comprises a mounting bracket or a drain outlet formed integrally with the one or more arcuate sections via the 3D printing manufacturing process, and wherein each arcuate section of the plurality of arcuate sections includes a wall separating the annular coolant intake passage from the annular coolant return passage and forming inner surfaces of each of the annular coolant intake passage and the annular coolant return passage, the wall formed via the 3D printing manufacturing process.

\* \* \* \* \*